(12) United States Patent
Kim et al.

(10) Patent No.: US 10,146,573 B2
(45) Date of Patent: Dec. 4, 2018

(54) METHOD AND APPARATUS FOR CONTROLLING POWER OUTPUT FROM ELECTRONIC DEVICE TO EXTERNAL ELECTRONIC DEVICE

(71) Applicant: Samsung Electronics Co., Ltd., Gyeonggi-do (KR)

(72) Inventors: Jin-Ik Kim, Seoul (KR); Jeong-Min Park, Gyeonggi-do (KR); Jae-Woong Chun, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 157 days.

(21) Appl. No.: 15/056,487

(22) Filed: Feb. 29, 2016

(65) Prior Publication Data
US 2016/0253218 A1 Sep. 1, 2016

(30) Foreign Application Priority Data
Feb. 27, 2015 (KR) ........................ 10-2015-0028487

(51) Int. Cl.
| | |
|---|---|
| *G06F 9/46* | (2006.01) |
| *H04L 29/08* | (2006.01) |
| *G06F 9/50* | (2006.01) |
| *G06F 9/48* | (2006.01) |
| *H04L 29/00* | (2006.01) |

(Continued)

(52) U.S. Cl.
CPC ............... *G06F 9/46* (2013.01); *G06F 9/466* (2013.01); *G06F 9/48* (2013.01); *G06F 9/50* (2013.01); *G06F 9/5094* (2013.01); *G06F 19/00* (2013.01); *G06F 19/3481* (2013.01); *H04L 29/00* (2013.01); *H04L 29/08* (2013.01); *H04L 29/0809* (2013.01); *H04L 29/08135* (2013.01); *H04L 29/08945* (2013.01); *H04L 29/08981* (2013.01); *A63B 24/0062* (2013.01); *A63B 2220/17* (2013.01); *A63B 2220/20* (2013.01);

(Continued)

(58) Field of Classification Search
CPC ... G06F 9/46; G06F 9/466; G06F 9/48; G06F 9/50; H04L 29/00; H04L 29/06; H04L 29/08; H04L 29/08135; H04L 29/0809; H04L 29/08945; H04L 29/08981
See application file for complete search history.

(56) References Cited

U.S. PATENT DOCUMENTS

| | | | |
|---|---|---|---|
| 2003/0182328 A1* | 9/2003 | Paquette | G06F 17/30575 |
| 2012/0317167 A1* | 12/2012 | Rahman | A61B 5/02055 |
| | | | 709/202 |

(Continued)

FOREIGN PATENT DOCUMENTS

| | | |
|---|---|---|
| JP | 2006-042850 | 2/2006 |
| KR | 10-2009-0053121 | 5/2009 |
| KR | 10-2014-0098555 | 8/2014 |

*Primary Examiner* — Charles M Swift
(74) *Attorney, Agent, or Firm* — The Farrell Law Firm, P.C.

(57) ABSTRACT

A method and an apparatus for batch processing of data between processors is provided. The method includes transmitting batch processing target information of at least one application to a second processor, by a first processor, transmitting, to the first processor, batch data generated to include at least a part of data acquired using one or more sensors based on the batch processing target information, by the second processor, and providing the received batch data received from the second processor to the at least one application, by the first processor.

26 Claims, 12 Drawing Sheets

(51) Int. Cl.
    *G06F 19/00*     (2018.01)
    *A63B 24/00*     (2006.01)
    *H04M 1/725*     (2006.01)

(52) U.S. Cl.
    CPC ..... *A63B 2230/75* (2013.01); *H04M 1/72569* (2013.01)

(56) References Cited

U.S. PATENT DOCUMENTS

| | | | |
|---|---|---|---|
| 2013/0262612 A1* | 10/2013 | Langas | G06F 3/0605 709/211 |
| 2014/0213189 A1 | 7/2014 | Kim et al. | |
| 2015/0180716 A1* | 6/2015 | Aminzade | H04L 41/0816 726/4 |
| 2015/0281364 A1* | 10/2015 | Connolly | H04L 67/12 709/217 |
| 2015/0324181 A1* | 11/2015 | Segal | G06F 9/5088 717/178 |
| 2016/0100004 A1* | 4/2016 | Anglin | H04L 67/1095 709/219 |

\* cited by examiner

METHOD AND APPARATUS FOR CONTROLLING POWER OUTPUT FROM ELECTRONIC DEVICE TO EXTERNAL ELECTRONIC DEVICE

PRIORITY

This application claims priority under 35 U.S.C. § 119(a) to Korean Application Serial No. 10-2015-0028487, which was filed in the Korean Intellectual Property Office on Feb. 27, 2015, the entire content of which is incorporated herein by reference.

BACKGROUND

1. Field of the Disclosure

The present disclosure generally relates to a method and apparatus for batch processing of data in an electronic device.

2. Description of the Related Art

An electronic device includes various sensors and, by using these sensors, an application which provides a user with a service such as fitness tracking, location tracking, monitoring by recognizing the peripheral situation of the electronic device and the current condition of the user or the electronic device, has been developed. For example, functions for tracking a moving path of an electronic device moving in real-time and displaying the moving path on a map on a display, such as a touch screen, can be provided. In addition, such an application is driven by interacting with a variety of sensors, which are installed in the electronic device, such as a GPS, an acceleration sensor, an angular velocity sensor, a temperature sensor, a pressure sensor, an atmospheric pressure sensor, a flow sensor, a geomagnetic sensor, an optical sensor, a sound sensor, and a taste sensor, where the sensors are either driven in the background while the other applications are driven or are driven simultaneously along with the other applications. Accordingly, the electronic device is required to quickly process a relatively large amount of data, and thus, demands a high-performance processor.

To reduce power consumption, the electronic device can use a data batching scheme in which data measured by various sensors is collected and stored for a predetermined time by a low power processor and data collected at a particular time is collectively transmitted by a high-performance processor.

Since electronic devices generally operate using a small sized battery having a small capacity, a problem of fast power consumption may occur when various applications are driven through a high-performance processor.

In addition, in a data batching scheme of transmitting data of various sensors collected by a low power processor through a high-performance processor when a fitness service for setting a goal regarding, for example, exercise time, exercise distance, a number of steps, or calories to burn by a user, and for notifying of success or failure in achieving the set goal in the fitness service of an application, the corresponding application inevitably receives, in real time, sensing data collected by the low power processor in order to check whether the exercise goal has been achieved; and when the application has the sensing data batch-processed at regular periods, there may exist a difference between the batch processing period and the time of the exercise goal, which may result in an inaccurate notification of the achievement of an exercise goal. As a result, an accurate notification service for the achievement of the exercise goal is needed.

SUMMARY

The present disclosure has been made to address at least the problems and disadvantages described above, and to provide at least the advantages described below.

Accordingly, an aspect of the present disclosure provides a method and an apparatus for batch processing of data wherein an electronic device performs batch processing of data, using a main processor, for sensing data constantly collected by a low power processor interacting with at least one sensor and thus power consumption can be minimized.

Accordingly, another aspect of the present disclosure provides a main processor which actively selects a time for batch processing of data to be performed by a low power processor and thus batch data can be provided in a batch processing period optimized for an application.

Accordingly, another aspect of the present disclosure provides a method whereby batch processing is available in an optimized batch processing period, reducing unnecessary usage of a main processor while providing a notification service for an exercise goal achievement of an application. In accordance with a aspect of the present disclosure, a method for batch processing of data between processors is provided. The method includes transmitting batch processing target information of at least one application to a second processor, by a first processor, transmitting, to the first processor, batch data generated to include at least a part of data acquired using one or more sensors based on the batch processing target information, by the second processor, and providing the received batch data received from the second processor to the at least one application, by the first processor.

In accordance with another aspect of the present disclosure, a first processor for batch processing of data between the first processor and a second processor is provided. The first processor includes at least one application; and a batch processing controller that transmits batch processing target information according to the at least one application to a second processor, receives, from the second processor, batch data generated to include at least a part of data acquired using one or more sensors based on the batch processing target information, and provides the received batch data to the at least one application.

In accordance with another aspect of the present disclosure, a second processor for batch processing of data between a first processor and the second processor is provided. The second processor includes a data module that stores data acquired by one or more sensors, and a batch data trigger module that receives, from the first processor, batch processing target information according to at least one application, and transmits, to the first processor, batch data generated to include at least a part of data acquired using one or more sensors based on the batch processing target information.

BRIEF DESCRIPTION OF THE DRAWINGS

The above and other aspects, features, and advantages of the present disclosure will be more apparent from the following detailed description taken in conjunction with the accompanying drawings, in which.

DETAILED DESCRIPTION

Figure 1:
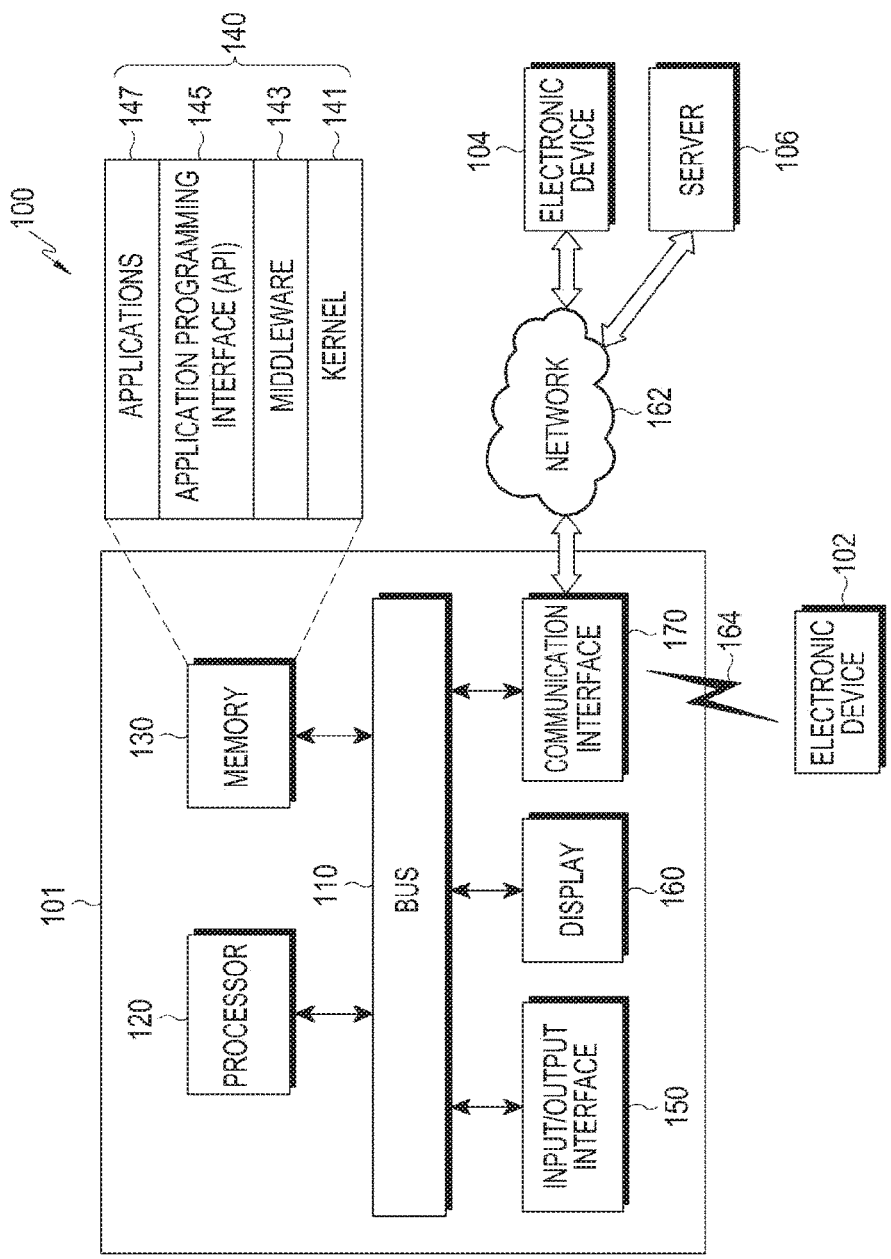
FIG. 1 is a block diagram illustrating a network environment including an electronic device, according to an embodiment of the present disclosure.

Hereinafter, various embodiments of the present disclosure will be described with reference to the accompanying drawings. However, it should be understood that there is no intent to limit the present disclosure to the particular forms disclosed herein; rather, the present disclosure should be construed to cover various modifications, equivalents, and/or alternatives of embodiments of the present disclosure. In describing the drawings, similar reference numerals may be used to designate similar constituent elements.

As used herein, the expressions "have", "may have", "include", and "may include" refer to the existence of a corresponding feature (e.g., numeral, function, operation, or constituent element such as component), and does not exclude one or more additional features.

In the present disclosure, the expressions "A or B", "at least one of A or/and B", and "one or more of A or/and B" may include all possible combinations of the items listed. For example, the expressions "A or B", "at least one of A and B", and "at least one of A or B" refer to all of (1) including A, (2) including B, or (3) including A and B.

Expressions, such as "a first", "a second", "the first", or "the second", used herein may modify various components regardless of the order and/or the importance but does not limit the corresponding components. For example, a first user device and a second user device indicate different user devices although both of them are user devices. For example, a first element may be referred to as a second element, and similarly, a second element may be referred to as a first element without departing from the scope of the present disclosure.

It should be understood that when an element (e.g., first element) is referred to as being (operatively or communicatively) "connected," or "coupled," to another element (e.g., second element), it may be directly connected or coupled directly to the other element or any other element (e.g., third element) may be interposed between the first and the second elements. In contrast, it may be understood that when an element (e.g., first element) is referred to as being "directly connected," or "directly coupled" to another element (second element), there are no element (e.g., third element) interposed between the first and the second elements.

The expression "configured to" used herein may be exchanged with, for example, "suitable for", "having the capacity to", "designed to", "adapted to", "made to", or "capable of" according to the situation. The term "configured to" may not necessarily imply "specifically designed to" in hardware. Alternatively, in some situations, the expression "device configured to" may mean that the device, together with other devices or components, "is able to". For example, the phrase "processor adapted (or configured) to perform A, B, and C" may mean a dedicated processor (e.g. embedded processor) only for performing the corresponding operations or a generic-purpose processor (e.g., central processing unit (CPU) or application processor (AP)) that can perform the corresponding operations by executing one or more software programs stored in a memory device.

The terms used herein are merely for the purpose of describing particular embodiments and are not intended to limit the scope of other embodiments. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the same meanings as the contextual meanings in the relevant field of art, and are not to be interpreted to have ideal or excessively formal meanings unless clearly defined in the present disclosure. In some cases, even terms defined in the present disclosure should not be interpreted to exclude embodiments of the present disclosure.

An electronic device according to various embodiments of the present disclosure may include at least one of a smart phone, a tablet Personal Computer (PC), a mobile phone, a video phone, an electronic book reader (e-book reader), a desktop PC, a laptop PC, a netbook computer, a workstation, a server, a Personal Digital Assistant (PDA), a Portable Multimedia Player (PMP), a MPEG-1 audio layer-3 (MP3) player, a mobile medical device, a camera, and a wearable device. The wearable device may include at least one of an accessory type (e.g., a watch, a ring, a bracelet, an anklet, a necklace, a glasses, a contact lens, or a Head-Mounted Device (HMD)), a fabric or clothing integrated type (e.g., an electronic clothing), a body-mounted type (e.g., a skin pad, or tattoo), and a bio-implantable type (e.g., an implantable circuit).

The electronic device may be a home appliance. The home appliance may include at least one of a television, a Digital Versatile Disk (DVD) player, an audio player, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ and PlayStation™), an electronic dictionary, an electronic key, a camcorder, and an electronic photo frame.

The electronic device may include at least one of various medical devices (e.g., various portable medical measuring devices (a blood glucose monitoring device, a heart rate monitoring device, a blood pressure measuring device, a body temperature measuring device, etc.), a Magnetic Resonance Angiography (MRA) machine, a Magnetic Resonance Imaging (MRI) machine, a Computed Tomography (CT) machine, and an ultrasonic machine), a navigation device, a Global Positioning System (GPS) receiver, an Event Data Recorder (EDR), a Flight Data Recorder (FDR), a Vehicle Infotainment Devices, an electronic device for a ship (e.g., a navigation device for a ship, and a gyro-compass), avionics, a security device, an automotive head unit, a robot for home or industry, an automatic teller's machine (ATM), a point of sales (POS) machine, or Internet of Things (IoT) device (e.g., a light bulb, various sensors, electric or gas meter, a sprinkler device, a fire alarm, a thermostat, a streetlamp, a toaster, a sporting goods, a hot water tank, a heater, a boiler, etc.).

The electronic device may include at least one of a part of furniture or a building/structure, an electronic board, an electronic signature receiving device, a projector, and various kinds of measuring instruments (e.g., a water meter, an electric meter, a gas meter, and a radio wave meter). The electronic device may be a combination of one or more of the aforementioned various devices. The electronic device may be a flexible device. Further, the electronic device is not limited to the aforementioned devices, and may include a new electronic device according to the development of new technology.

Hereinafter, an electronic device according to various embodiments will be described with reference to the accompanying drawings. As used herein, the term "user" may indicate a person who uses an electronic device or may indicate a device (e.g., an artificial intelligence electronic device) that uses an electronic device.

FIG. 1 is a block diagram illustrating a network environment including an electronic device, according to an embodiment of the present disclosure.

Referring to FIG. 1, an electronic device 101 within a network environment 100 is provided. The electronic device 101 includes a bus 110, a processor 120, a memory 130, an input/output interface 150, a display 160, and a communication interface 170. In any embodiment, the electronic device 101 may omit at least some of the above components or further include other components.

The bus 110 includes a circuit for connecting the components of the electronic device 101 and transmitting communication between the components (for example, control messages and/or data).

The processor 120 may include at least one of a central processing unit (CPU), an application processor (AP), a supplementary processor (SP), and a communication processor (CP). The processor 120 controls one or more other components of the electronic device 101 and/or processes an operation or data related to communication.

The memory 130 includes a volatile memory and/or a non-volatile memory. The memory 130 stores instructions or data related to at least one other component of the electronic device 101. The memory 130 may store software and/or a program 140.

The program 140 includes a kernel 141, middleware 143, an Application Programming Interface (API) 145, and/or an applications 147. At least some of the kernel 141, the middleware 143, and the API 145 may be referred to as an Operating System (OS).

The kernel 141 controls or manages system resources (for example, the bus 110, the processor 120, and the memory 130) which are used to execute an operation or a function implemented in the other programs 140 (for example, the middleware 143, the API 145, and the application programs 147). Furthermore, the kernel 141 may provide an interface through which the middleware 143, the API 145, or the application program 147 may access individual components of the electronic device 101 to control or manage system resources.

The middleware 143 serves as a relay for allowing the API 145 or the applications 147 to communicate with the kernel 141 to exchange data. In addition, the middleware 143 processes one or more operation requests received from the applications 147 according to priority requests. For example, the middleware 143 assigns a priority request to one or more applications in the applications 147 for using a system resource (for example, the bus 110, the processor 120, or the memory 130) of the electronic device 101. The middleware 143 may perform scheduling or loading balancing on the one or more task requests by processing the one or more task requests according to the priorities assigned thereto.

The API 145, which is an interface for controlling a function provided from the kernel 141 or the middleware 143 by the applications 147, includes at least one interface or function (e.g., a command) for file controlling, window controlling, image processing, text controlling, etc.

The input/output interface 150 serves as an interface that transfers instructions or data, which is input from a user or an external device, to another component(s) of the electronic device 101. Further, the input/output interface 150 outputs instructions or data received from another component(s) of the electronic device 101 to a user or another external device.

Examples of the display 160 includes a Liquid Crystal Display (LCD), a Light-Emitting Diode (LED) display, an Organic Light-Emitting Diode (OLED) display, a Micro-ElectroMechanical Systems (MEMS) display, and an electronic paper display. The display 160 displays various types of contents (for example, text, images, videos, icons, or symbols) to users. The display 160 may include a touch screen and receive, for example, a touch input, a gesture input, a proximity input, or a hovering input using an electronic pen or a user's body part.

The communication interface 170 sets communication between the electronic device 101 and an external device, such as, a first external electronic device 102, a second external electronic device 104, or a server 106. For example, the communication interface 170 may be connected to a network 162 through wireless or wired communication to communicate with the second external electronic device 104 or the server 106.

The wireless communication may use at least one of Long Term Evolution (LTE), LTE-Advance (LTE-A), Code Division Multiple Access (CDMA), Wideband CDMA (WCDMA), Universal Mobile Telecommunications System (UMTS), WiBro (Wireless Broadband), and Global System for Mobile Communications (GSM), as a cellular communication protocol. In addition, the wireless communication may include short range communication 164.

The short-range communication 164 may be performed by using at least one of, for example, Wi-Fi, Bluetooth, Near Field Communication (NFC), and Global Navigation Satellite System (GNSS). The GNSS may include at least one of a Global Positioning System (GPS), a Global Navigation Satellite System (Glonass), a Beidou Navigation Satellite System, and a European Global Satellite-based Navigation System (Galileo), according to a use area, a bandwidth, etc. Hereinafter, in the present disclosure, the "GPS" may be interchangeably used with the "GNSS".

The wired communication may include at least one of a Universal Serial Bus (USB), a High Definition Multimedia Interface (HDMI), Recommended Standard 232 (RS-232), and a Plain Old Telephone Service (POTS).

The network 162 may include at least one of communication networks such as a computer network (for example, a LAN or a WAN), the Internet, and a telephone network.

Each of the first external electronic device 102 and the second external electronic device 104 may be a device which is the same as or different from the electronic device 101. The server 106 may include a group of one or more servers. According to various embodiments, all or some of the operations performed by the electronic device 101 may be performed by another electronic device or a plurality of electronic devices, such as the first external electronic device 102, the second external electronic device 104, or the server 106. When the electronic device 101 should perform some functions or services automatically or by request, the electronic device 101 may make a request for performing at least some of the functions related to the functions or services to the first external electronic device 102, the second external electronic device 104, or the server 106 instead of performing the functions or services by itself. The other electronic device may carry out the requested function or the additional function and transfer the result, obtained by carrying out the function, to the electronic device 101. The electronic device 101 may provide the requested functions or services based on the received result as it is or after additionally processing the received result. To achieve this cloud computing, distributed computing, or client-server computing technology may be used.

The processor 120 is a main processor which includes a high performance CPU for displaying a user interface (UI) and a complicated calculation, an application processor (AP) which is a high power processor having a large capacity memory, and a supplementary processor (SP) which is a low power processor having a low performance CPU and small capacity memory relative to the application processor.

The application processor can process at least a part of information acquired from other elements (for example, at least one from the supplementary processor, the memory 130, the input/output interface 150, the communication interface 170, etc.) and use such elements in various methods. For example, the application processor can control at least a part of the function of the electronic device 101 for allowing the electronic device 101 to interwork with the other electronic devices. The application processor may be integrated with the processor 120 or the communication interface 170. At least one configuration of the application processor may be included in the server 106 and may support at least one operation implemented in the application processor from the server 106. The application processor may have the same configuration as the processor 120 and the terms referring thereto which are "a main processor", "a first processor", "processor one", "a main processing device", "a CPU", "a high power processor", "a high end processor", and "an AP" may refer to the same processor.

The supplementary processor (SP), which is provided separately from the application processor and is a processor configured to be optimized for a low power operation, may be included in the processor 120, have less computing power than the application processor, include more limited interfaces and memory to relatively minimize power consumption, and therefore be configured to enable continuous operations. The supplementary processor interacts with at least one sensor (e.g., an acceleration sensor, a gyro sensor, a magnetic sensor, etc.) to collect sensing data, and calculates context data which indicates a user's activity state (e.g., sitting, standing, walking, running, etc.) using the sensed data. Terms referring to the supplementary processor, such as "a sub processor", "a second processor", "processor two", "a sensor HUB", "a micro controller", "a sensing processor", and "an SP", may refer to the same processor.

The application processor transmits batch processing target information, according to one or more applications 147, to the supplementary processor. The application 147 may be an application which can provide one or more functions related to health care (e.g., measuring the amount of exercise, blood sugar level, calories, etc.), providing environmental information (e.g., providing information on atmospheric pressure, humidity, temperature, etc.), situational awareness (e.g., providing location tracking, activity status, etc.), etc. In addition, the application 147, as a part of health care, can provide an exercise goal service which can provide a notification to a user when the user achieves the exercise goal set by the user as the user performs the exercise. Further, the application 147 receives, from the user, a goal which is set relating to at least one of exercise time, exercise distance, number of steps, calories to burn, exercise state recognition, and types of exercise (e.g., walking, running, etc.). The application 147 determines whether the set goal is achieved, and provides notification service to the user. Also, the application 147 transmits, to the application processor, information on the exercise goal in order to differentiate the batch processing period in a general situation from the batch processing period in the situation which is close to the exercise goal according to a type of data acquired by at least one sensor for performing an operation and for providing the exercise goal service.

In addition, the application processor configures batch processing target information including at least one of a type of data required for batch processing of each of the applications 147 according to the exercise goal service, a type of target data required for determining a batch processing mode according to the exercise goal service, and a batch processing trigger condition for determining the batch processing mode according to the acquisition state of the target data, of one or more applications 147, transmits the batch processing target information to a supplementary processor, and requests the batch data to be batch-processed wherein the batch data is configured to be in the batch processing mode according to the data state acquired on the basis of the batch processing target information from the supplementary processor.

The batch processing target information is information about data required for batch processing of the application 147 and includes at least one of a type of data to be batch-processed, a type of target data required for determining a batch processing mode, and a batch processing trigger condition for determining the batch processing mode according to the acquisition state of the target data.

For example, the batch processing target information includes sensing data collected by at least one sensor required for performing an operation of the application 147 and context data calculated using the sensing data. Further, in the context data, particular data required for determining a proper batch processing period for providing the exercise goal service of the application 147 can be selected as target data. The sensing data and context data is acquired by the supplementary processor. In addition, the context data is information which is calculated using at least one piece of sensing data acquired by a sensor, and includes information such as, distance, velocity, altitude, calories, number of steps, exercise state recognition, etc. For example, context data corresponding to the exercise state recognition of a user is data which has determined the exercise state of the user by comparing the sensing data acquired by an acceleration sensor, a gyro sensor, a magnetic sensor, etc. with a waveform of the characteristic pattern according to each of preset exercise states. That is, information indicating the user's exercise state (walking, running, biking, etc.) may be obtained from patterns of a period of waveform, intensity, vibration, etc., of the sensing data acquired by the sensor. Further, the context data is information which can be acquired through a simple operation of the sensing data (e.g., an atmospheric pressure value) acquired by an atmospheric pressure sensor like altitude information which cannot be acquired only by untreated (raw) sensing data, and such information may also be utilized for deriving information displaying the exercise state such as mountain climbing according to the change in altitude.

In addition, the target data is information which has been selected for particular context data required for determining a proper batch processing period for providing the exercise goal service of the application 147. For example, the target data includes context data corresponding to exercise state recognition information which informs of the user's exercise state, such as walking, running, biking, the number of steps which is used for calculating the distance or consumed calories according to exercise, and altitude information which informs the change in altitude according to an exercise like mountain climbing.

Further, the batch processing trigger condition relates to a condition which enables the determination of a batch processing mode for setting a proper batch processing period for providing the exercise goal service of the application 147.

For example, the batch processing trigger condition may indicate that the batch processing mode is to be determined based on the acquisition state of the target data. In this case, if the exercise goal of the application 147 is set to provide a notification service when a particular exercise starts, the context data corresponding to exercise state recognition information, such as walking, running, and biking, can be selected as target data, and when acquisition of the target data is identified, it can be immediately recognized that the user has started the exercise corresponding to the target data, and thus the batch processing mode is switched to a mode in which batch data is provided in real-time.

In another example, the batch processing trigger condition may indicate that the batch processing mode is to be determined based on the accumulated time according to the acquisition state of the target data. In this case, when the exercise goal of the application 147 sets goal values of predetermined time, distance, number of steps, and calories to burn after beginning an exercise, such as walking, and is set to provide a notification service when the corresponding goal is achieved: the context data corresponding to exercise state recognition information of walking may be selected as target data. A timer is driven according to the acquisition of the target data to check the accumulated time, and the batch processing trigger condition switches the batch processing mode to a mode in which batch data is provided in real-time by determining whether the accumulated time meets the threshold value defined as the accumulated time which appears when the user continues exercising until the time reaches close to the set goal.

In another example, the batch processing trigger condition may indicate that the batch processing mode is to be determined based on the amount of accumulated data according to the acquisition state of the target data. In this case, the batch processing trigger condition uses substantially the same scheme applied in the batch processing trigger condition using the accumulated time except for the change from the accumulated time to the amount of accumulated data and switches the batch processing mode to a mode in which batch data is provided in real-time.

In another example, the batch processing trigger condition may indicate that the batch processing mode is to be determined based on the number of pieces of accumulated batch data according to batch processing of acquired data. In this case, the batch processing trigger condition switches the batch processing mode to a mode in which batch data is provided in real-time by determining the time to switch a batch processing mode, after identifying the acquisition of target data, using the change in number of batch-processed times without regard to the acquisition state of target data.

The batch processing trigger condition can further determine a batch processing mode using a piece of target data, but the present disclosure is not limited thereto and a batch processing mode can be determined using multiple pieces of target data. For example, if the exercise goal of the application 147 is set to provide a goal notification service regarding exercise distance when the exercise condition is not limited to one, and involves walking and running performed together, the context data corresponding to the exercise state recognition information of walking and the context data corresponding to the exercise state recognition information of running both can be selected as target data, and it is preferable that the accumulated time or the threshold value of the amount of accumulated data according to the acquisition state of two such pieces of the target data are set to be different from each other. This is to accurately determine the switching time of a batch processing mode even when the two exercises are performed together, because the range of change in exercise distance by running and the range of change in exercise distance by walking are different from each other.

A supplementary processor selects and acquires data on the basis of the received batch processing target information determines a batch processing mode according to the acquisition state of data configures batch data according to the determined batch processing mode and transmits the batch data to the application processor.

The supplementary processor may identify a type of data included in the batch processing target information received from the application processor and acquire data corresponding to the identified type of data only. For example, based on the batch processing target information, the supplementary processor activates a sensor which requires acquisition of sensing data in at least one sensor provided in an electronic device 101, and stores sensing data acquired from an activated sensor. In addition, the supplementary processor, when a type of data includes context data, performs an arithmetic operation for calculating the corresponding context data, calculates context data using sensing data required for calculating context data, and selects and stores target data required for determining the batch processing mode in the context data. Further, the supplementary processor can identify the received batch processing target information, and in accordance with the state of the acquired data on the basis of the identified batch processing target information, determine a batch processing mode for setting a proper batch processing period according to the exercise goal service of the application 147.

The batch processing mode includes a basic batch processing mode and a batch processing switching mode.

The basic batch processing mode is preset and batch processing may be available by at least one of a batch processing period, reaching a threshold capacity of a memory, receiving a signal for requesting a batch process, and a transmission capacity and speed between processors, in a general situation.

The batch processing switching mode is set by selectively changing a batch processing period and the amount of data for batch processing, in which a batch processing period can be set to be short or gradually become shorter while the amount of data for batch processing can be set to be small or gradually become smaller.

The supplementary processor identifies the received batch processing target information, and in accordance with the batch processing trigger condition included in the identified batch processing target information, determine a batch processing mode for determining a proper batch processing period for providing the exercise goal service of the application 147.

For example, in a case where the batch processing trigger condition indicates to determine the batch processing mode by success or failure of the acquisition of the target data, the context data corresponding to exercise state recognition information, such as walking, running, and biking, may be selected as target data, when the acquisition of the target data is identified during the process of data acquisition, the batch processing mode is switched to a mode in which batch data is provided in real-time, data which has been acquired and stored so far may be set as batch data. The set batch data is transmitted to the application processor, while the data acquired thereafter is immediately set as batch data and transmitted to the application processor. Such a process continues until a goal notification of the application for providing the exercise goal service in the application processor is provided.

In another example, in a case where the batch processing trigger condition indicates to determine the batch processing mode based on the accumulated time according to the acquisition state of the target data, the context data corresponding to exercise state recognition information of walking may be selected as target data, when the acquisition of the target data is identified during the acquisition process of data, a timer is driven according to the acquisition state of the target data to check the accumulated time. It is then determined whether the accumulated time meets the threshold value defined as the accumulated time which appears when the user continues exercising until the time reaches close to the set goal. In this case, the batch processing mode is switched to a mode in which batch data is provided in real-time, data which has been acquired and stored so far is set as batch data, and the set batch data is transmitted to the application processor, while the data acquired thereafter is immediately set as batch data and transmitted to the application processor. Such a process continues until a goal notification of the application for providing the exercise goal service in the application processor is provided.

In another example, in a case where the batch processing trigger condition indicates to determine the batch processing mode based on the amount of accumulated data according to the acquisition state of the target data, batch processing is performed by switching the batch processing mode using substantially the same scheme applied in the batch processing trigger condition using the accumulated time except for the change from the accumulated time to the amount of accumulated data.

In another example, in a case where the batch processing trigger condition indicates to determine the batch processing mode based on the number of pieces of accumulated batch data according to the acquisition state of the target data, the switching time of a batch processing mode is determined using the change in number of batch-processed times without regard to the acquisition state of the target data after identifying the acquisition of target data and the batch processing mode may be switched accordingly to perform batch processing.

The application processor batch-processes the received batch data on one or more applications 147.

For example, the application processor provides batch data configured according to the batch processing mode determined by the supplementary processor to each of applications 147. For example, when batch processing is performed in a basic batch processing mode by the supplementary processor, the application processor performs batch processing on an application 147 through an ordinary scheme. When batch processing is performed in a batch processing switching mode by the supplementary processor, the application processor performs batch processing on an application 147 in real-time, and accordingly, the application 147 can provide an exercise goal service which can provide a notification of a goal achievement to a user when the user has accomplished a preset exercise goal. When the goal notification by the exercise goal service of the application 147 is provided, the application processor indicates a switch of the batch processing mode to the supplementary processor. At this point, the switch of the batch processing mode can be either switched back to a basic batch processing mode or switched to a batch processing switching mode in which a modified batch processing period or modified amount of data for batch processing is set.

Figure 2:
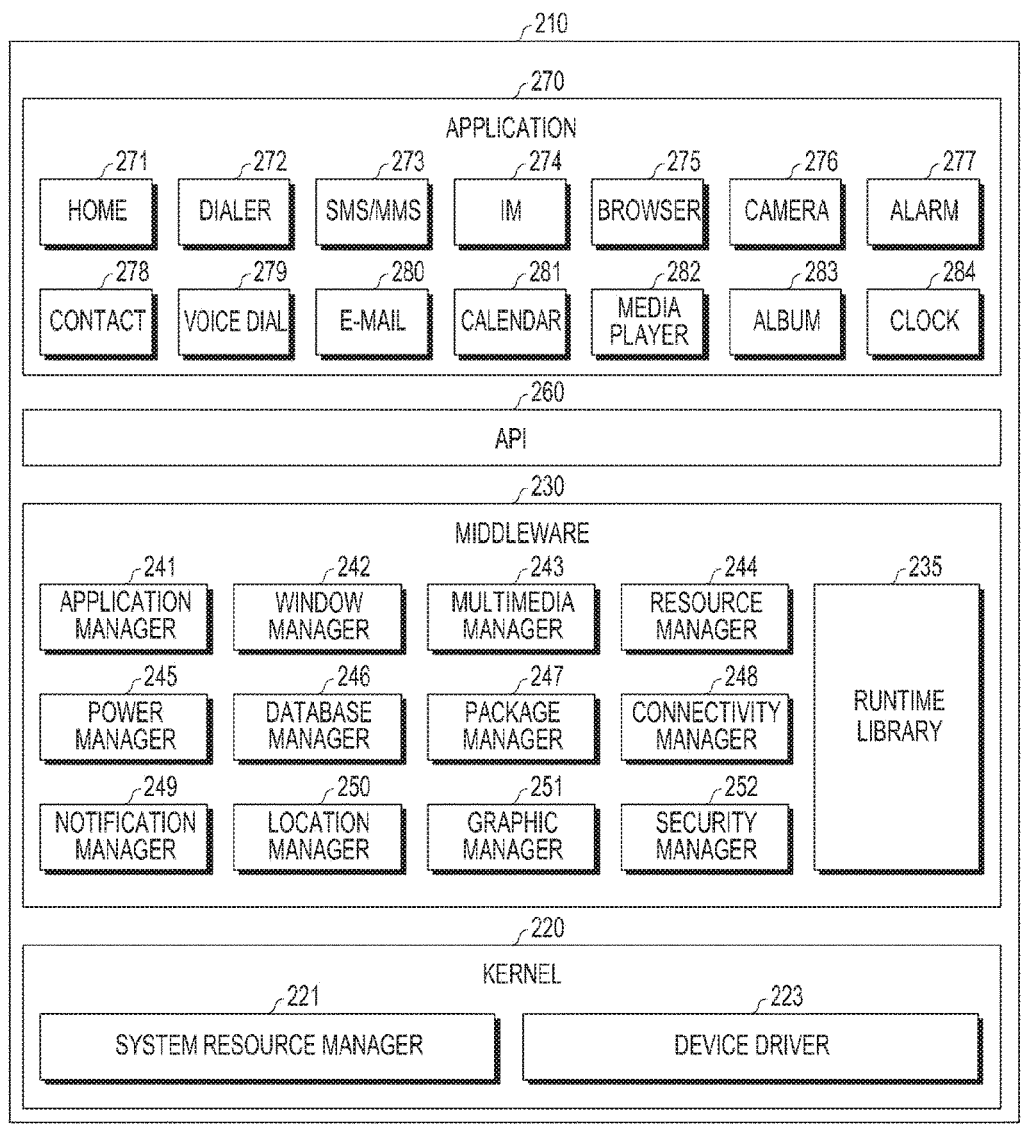
FIG. 2 is a block diagram illustrating a program module, according to an embodiment of the present disclosure.

FIG. 2 is a block diagram illustrating a program module, according to an embodiment of the present disclosure.

Referring to FIG. 2, a program module 210 (for example, the program 140) may include an Operating System (OS) for controlling resources related to the electronic device 101 and/or various applications 147 executed in the operating system. The operating system may be, for example, Android, iOS, Windows, Symbian, Tizen, Bada, etc.

The programming module 210 includes a kernel 220, middleware 230, an Application Programming Interface (API) 260, and applications 270. At least a part of the programming module 210 may be preloaded on an electronic device or downloaded from a server. The kernel 220 (for example, the kernel 141) includes a system resource manager 221 and a device driver 223. The system resource manager 221 controls, allocates, or collects the system resources. According to an embodiment, the system resource manager 221 includes a process manager, a memory manager, or a file system manager. The device driver 223 includes, for example, a display driver, a camera driver, a Bluetooth driver, a shared-memory driver, a USB driver, a keypad driver, a WIFI driver, an audio driver, or an Inter-Process Communication (IPC) driver.

The middleware 230 (for example, the middleware 143) provides a common function required by the applications 270 or provides various functions to the applications 270 through the API 260 so that the applications 270 may efficiently use limited system resources of the electronic device 101. The middleware 230 may include, for example, a runtime library 235, an application manager 241, a window manager 242, a multimedia manager 243, a resource manager 244, a power manager 245, a database manager 246, a package manager 247, a connectivity manager 248, a notification manager 249, a location manager 250, a graphic manager 251, and a security manager 252.

The run time library 235 includes a library module that a compiler uses in order to add new functions through a programming language while an application of the applications 270 is executed. The run time library 235 performs input/output management, memory management, or an arithmetic function.

The application manager 241 manages a life cycle of at least one application among the applications 270.

The window manager 242 manages a GUI resource used in a screen of the electronic device 101.

The multimedia manager 243 detects a format required for reproducing various media files and encodes or decodes a media file using a codec appropriate for the corresponding format.

The resource manager 244 manages resources such as a source code, a memory, or a storage space of at least one application among the applications 270.

The power manager 245 operates together with a Basic Input/Output System (BIOS), so as to manage a battery or power of the electronic device 101 and provides power information required for the operation of the electronic device 101.

The database manager 246 generates, searches for, or changes a database to be used by at least one of the applications 270.

The package manager 247 manages the installation or updating of the applications 270 distributed in the form of a package file.

The connectivity manager 248 manages wireless connections, such as Wi-Fi or Bluetooth.

The notification manager 249 displays or notifies a user of the electronic device 101 of an event such as a received message, an appointment, a proximity notification, etc. without disturbance.

The location manager 250 manages location information of the electronic device 101.

The graphic manager 251 manages graphic effects to be provided to the user and user interfaces related to the graphic effects.

The security manager 252 provides various security functions required for system security or user authentication.

When the electronic device 101 has a call function, the middleware 230 may further include a telephony manager for managing a voice call function or a video call function of the electronic device.

The middleware 230 may include a middleware module for forming a combination of various functions of the aforementioned components. The middleware 230 may provide a module specialized for each type of operating system in order to provide a differentiated function. In addition, a few existing components may be dynamically removed from the middleware 230, or new components may be added to the middleware 230.

The API 260 (for example, the API 145), which is a set of programming functions, may be provided in a different configuration for each operating system. For example, in the case of Android or iOS, one API set may be provided for each platform. In the case of Tizen, two or more API sets may be provided for each platform. The API 260 may be preloaded on the electronic device 101, or may be downloaded from the first external electronic device 102, the second external electronic device 104, or the server 106. The applications 270 (for example, the applications 147) may include, for example, a home application 271, a dialer application 272, an SMS/MMS application 273, an Instant Message (IM) application 274, a browser application 275, a camera application 276, an alarm application 277, a contact information application 278, a voice dial application 279, and e-mail application 280, a calendar application 281, a media player application 282, an album application 283, and a clock application 284. The applications 270 may further include a health care application (for example, an application for measuring an amount of exercise or blood sugar) and an environmental information application (for example, an application for providing atmospheric pressure, humidity, or temperature information).

The applications 270 may include an application supporting information exchange between the electronic device 101 and an external electronic device 102 or 104. The information exchange application may include a notification relay application for transmitting predetermined information to as external electronic device, or a device management application for managing the external electronic device.

The notification relay application transfers to the external electronic device, notification information generated from other applications of the electronic device 101 (for example, the SMS/MMS application 273, the e-mail application 280, the health management application, or the environmental information application). Further, the notification relay application receives notification information from an external electronic device and provides the received notification information to a user.

The device management application manages (for example installs, deletes, or updates) a function for at least a part of the external electronic device communicating with the electronic device 101 (for example, turning on/off the first external electronic device 102 or the second external electronic device 104 itself (or some elements thereof) or adjusting brightness (or resolution) of a display, applications executed in the external electronic device, or services provided from the external electronic device (for example, a telephone call service or a message service).

The applications 270 may include an application (e.g., a health care application of a mobile medical device or the like) designated according to an attribute of the first external electronic device 102 or the second external electronic device 104.

The applications 270 may include an application received from the external electronic device.

The applications 270 may include a preloaded application or a third party application which can be downloaded from the server 106.

Names of the elements of the program module 210, according to the above-described embodiments of the present invention, may change depending on the type of OS.

At least some of the program module 210 may be implemented in software, firmware, hardware, or a combination thereof. At least some of the program module 210 may be implemented or executed by the processor 120. At least some of the program module 210 may include a module, program, routine, sets of instructions, process, or the like for performing one or more functions.

The term "module" as used herein may mean a unit including one of hardware, software, and firmware or a combination of them. The "module" may be interchangeably used with the term "unit", "logic", "logical block", "component", or "circuit". The "module" may be a minimum unit of an integrated component element or a part thereof. The "module" may be a minimum unit for performing one or more functions or a part thereof. The "module" may be mechanically or electronically implemented. For example, the "module" may include at least one of an Application-Specific Integrated Circuit (ASIC) chip, a Field-Programmable Gate Arrays (FPGA), and a programmable-logic device for performing operations which has been known or are to be developed hereinafter.

At least some of the devices (for example, modules or functions thereof) or the method (for example, operations) according to the present disclosure may be implemented by a command stored in a non-transitory computer-readable storage medium in a programming module form. When the command is executed by one or more processors, such as the processor 120, the one or more processors may execute a function corresponding to the command. The computer-readable storage medium may be the memory 130.

The computer readable recoding medium may include a hard disk, a floppy disk, magnetic media (e.g., a magnetic tape), optical media (e.g., a Compact Disc Read Only Memory (CD-ROM) and a Digital Versatile Disc (DVD)), magneto-optical media (e.g., a floptical disk), a hardware device (e.g., a Read Only Memory (ROM), a Random Access Memory (RAM), a flash memory), and the like. In addition, the program instructions may include high-level language codes, which can be executed in a computer by using an interpreter, as well as machine codes made by a compiler. The aforementioned hardware device may be configured to operate as one or more software modules in order to perform the operation of the present invention, and vice versa.

The programming module, according to the present disclosure, may include one or more of the aforementioned components or may further include other additional components, or some of the aforementioned components may be omitted. Operations executed by a module, a programming module, or other component elements may be executed sequentially, in parallel, repeatedly, or in a heuristic manner. Further, some operations may be executed according to another order or may be omitted, or other operations may be added.

Figure 3:
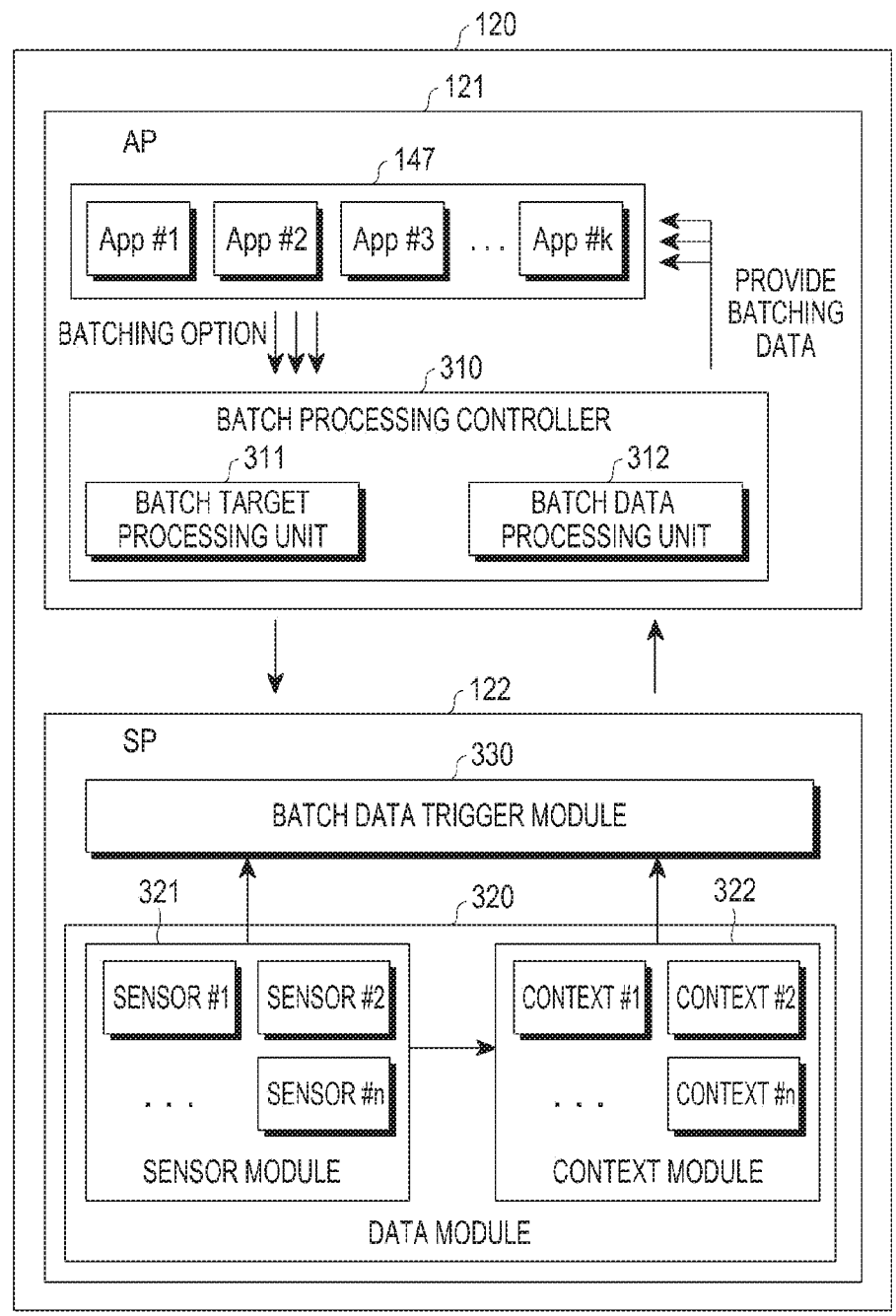
FIG. 3 is a block diagram illustrating a processor of an electronic device for batch processing of data, according to an embodiment of the present disclosure.

FIG. 3 is a block diagram illustrating a processor of an electronic device for batch processing of data, according to an embodiment of the present disclosure.

Referring to FIG. 3, a processor 120 of electronic device 101 is provided. The processor 120 includes an application processor 121 and a supplementary processor 122. The electronic device 101 actively selects a batch processing period between the application processor 121 and the supplementary processor (SP) 122 and enables a batch process. The application processor 121 includes one or more applications 147, such as App #1, App #2, App # . . . App #k, and a batch processing controller 310. The supplementary processor 122 includes a data module 320 and a batch data trigger module 330.

One of the applications 147 may be an application which provides one or more functions related to health care (e.g., measuring the amount of exercise, blood sugar level, calories, etc.), providing environmental information (e.g., providing information on atmospheric pressure, humidity, temperature, etc.), situational awareness (e.g., providing location tracking, activity status, etc.), and the like. The application 147, which provides the health care function, provides an exercise goal service which can provide a notification service to a user when the user achieves the exercise goal set by the user as the user performs the exercise. In this case, the application 147 receives, from the user, a goal which is set relating to at least one of exercise time, exercise distance, number of steps, calories to burn, exercise state recognition, types of exercise (e.g., walking, running, etc.). The application 147 determines whether the set goal is achieved, and provides the notification service to the user. The application 147 may require data acquired by at least one sensor in order to perform an operation to provide the above described functions. The application 147 transmits, to the batch processing controller 310, information about the exercise goal set by the user in order to differentiate the batch processing period in a general situation from the batch processing period in a situation which is close to the exercise goal for providing a type of data required for batch processing of the corresponding application 147 and/or exercise goal service.

The batch processing controller 310 includes a batch target processing unit 311 and a batch data processing unit 312.

The batch target processing unit 311 of the batch processing controller 310 receives, from the one or more applications 147, information about an exercise goal set by a user for providing the type of data required for batch processing and/or the exercise goal service, determines batch processing target information according to one or more applications 147, and transmits the determined batch processing target information to the batch data trigger module 330 of the supplementary processor 122.

The batch processing target information is information about data required for batch processing of the application 147 and includes at least one of a type of data to be batch-processed, a type of target data required for determining a batch processing mode, and a batch processing trigger condition for determining the batch processing mode according to the acquisition state of the target data.

The batch processing target information includes sensing data, collected from at least one sensor, required for performing an operation of the application 147 and/or a type of context data calculated using the sensing data. In the context data, particular data required for determining a proper batch processing period for providing the exercise goal service of the application 147 can be selected as target data. The sensing data and context data is acquired by the supplementary processor. The context data is information which is calculated using at least one piece of sensing data acquired by a sensor. The context data includes information such as distance, velocity, altitude, calories, number of steps, exercise state recognition, etc. For example, context data corresponding to the exercise state recognition of a user may be data indicating the exercise state of the user, which has been determined by comparing the sensing data acquired by a sensor, such as an acceleration sensor, a gyro sensor, a magnetic sensor, etc., with a waveform of the characteristic pattern according to each of preset exercise states. That is, information indicating the user's exercise state (walking, running, biking, etc.) may be obtained from patterns of a period of waveform, intensity, vibration, etc. of the sensing data acquired by the sensor. Further, the context data may be information which can be acquired through a simple operation of the sensing data (e.g., an atmospheric pressure value) acquired by an atmospheric pressure sensor, such as altitude information which cannot be acquired only by untreated (raw) sensing data, and such information may also be utilized for deriving information displaying the exercise state of the user, such as mountain climbing according to the change in altitude.

The target data may be information which has been selected for particular context data required for determining a proper batch processing period for providing the exercise goal service of the application 147. For example, the target data may includes context data corresponding to exercise state recognition information which informs of the user's exercise state, such as walking, running, biking; the number of steps which is used for calculating the distance or consumed calories according to exercise; and altitude information which informs the change in altitude according to an exercise like mountain climbing.

Further, the batch processing trigger condition relates to a condition which enables the determination of a batch processing mode for setting a proper batch processing period for providing the exercise goal service of the application 147. The batch processing trigger condition may be information which indicates that the batch processing mode is to be determined according to the acquisition state of the target data. For example, the batch processing trigger condition may indicate that the batch processing mode is to be determined by the acquisition state of the target data. In this case, if the exercise goal of the application 147 is set to provide a notification service when a particular exercise starts, the context data corresponding to exercise state recognition information like walking, running, and biking can be selected as target data, and when acquisition of the target data is identified, it can be immediately recognized that the user has started the exercise corresponding to the target data, and thus the batch processing mode is switched to a mode in which batch data is provided in real-time.

In another example, the batch processing trigger condition may indicate that the batch processing mode is to be determined based on the accumulated time according to the acquisition state of the target data. In the case, where the exercise goal of the application 147 sets goal values of a predetermined time, distance, number of steps, and calories to burn after beginning an exercise such as walking, and is set to provide a notification service when the corresponding goal is achieved, the context data corresponding to exercise state recognition information of walking may be selected as target data. A timer is driven according to the acquisition state of the target data to check the accumulated time, and the batch processing trigger condition switches the batch processing mode to a mode in which batch data is provided in real-time by determining whether the accumulated time meets the threshold value defined as the accumulated time which appears when the user continues exercising until the time reaches close to the set goal.

In another example, the batch processing trigger condition can indicate to determine the batch processing mode based on the amount of accumulated data according to the acquisition state of the target data. In this case, the batch processing trigger condition uses substantially the same scheme applied in the batch processing trigger condition using the accumulated time except for the change from the accumulated time to the amount of accumulated data and can switch the batch processing mode to a mode in which batch data is provided in real-time.

In another example, the batch processing trigger condition may indicate that the batch processing mode is determined based on the number of pieces of accumulated batch data according to batch processing of acquired data. In this case, the batch processing trigger condition switches the batch processing mode to a mode in which batch data is provided in real-time by determining the time to switch a batch processing mode, after identifying the acquisition of target data, using the change in the number of batch-processed times without regard to the acquisition state of target data.

Additionally, the batch processing trigger condition can determine a batch processing mode using a piece of target data, however, the present disclosure is not limited thereto and a batch processing mode can be determined using multiple pieces of target data. For example, if the exercise goal of the application 147 is set to provide a goal notification service regarding an exercise distance when the exercise condition is not limited to one and involves walking and running performed together, the context data corresponding to the exercise state recognition information of walking and the context data corresponding to the exercise state recognition information of running both can be selected as target data, and it is preferable that the accumulated time or the threshold value of the amount of accumulated data according to the acquisition state of two such pieces of target data are set to be different from each other. This is to accurately determine the switching time of a batch processing mode even when the two exercises are performed together, because the range of change in exercise distance by running and the range of change in exercise distance by walking are different from each other.

The batch data processing unit 312 of the batch processing controller 310 provides batch data received from a batch data trigger module 330 of the supplementary processor 122 to the one or more applications 147.

The batch data processing unit 312 can rearrange batch data received from the batch data trigger module 330 according to a type of data required for the one or more applications 147 and provide the rearranged data to each of applications 147.

The batch data processing unit 312 provides batch data received from the batch data trigger module 330 to the one or more applications 147. When batch processing is performed in a basic batch processing mode in the batch data trigger module 330, received batch data is provided to the application 147 in predetermined batch processing periods. When batch processing is performed in a batch processing switching mode in the batch data trigger module 330, the batch data processing unit 312 provides batch data received in real-time to the application 147, when the batch processing switching mode is set, for example, to have a batch processing period set in real-time. Accordingly, the application 147 can provide an exercise goal service which can provide a notification of a goal achievement to a user when the user has accomplished a preset exercise goal. When a goal notification by the exercise goal service of the application 147 is provided, the batch data processing unit 312 can pass through the batch target processing unit 311 or can bypass the batch target processing unit 311 and directly indicate the switch of the batch processing mode to the batch data trigger module 330. The switch of the batch processing mode can be either switched back to a basic batch processing mode or switched to a batch processing switching mode in which a modified batch processing period or modified amount of data for batch processing is set.

As described, the supplementary processor 122 includes a data module 320 and a batch data trigger module 330.

The data module 320 includes a sensor module 321 and a context module 322.

The sensor module 321 of the data module 320 includes one or more sensors (Sensor #1, Sensor #2, Sensor #n). Such sensors (Sensor #1, Sensor #2, Sensor#n) may include a gesture sensor, a gyro sensor, an atmospheric pressure sensor, a magnetic sensor, an acceleration sensor, a grip sensor, a proximity sensor, a color sensor (for example, RGB (red, green, blue) sensor), a biometric sensor, a temperature/humidity sensor, an illumination sensor, a ultra violet (UV)

sensor, smell sensor (E-nose sensor), EMG sensor (electromyography sensor), an electroencephalogram (EEG) sensor, an electrocardiogram (ECG) sensor, an infrared (IR) sensor, an iris sensor, and/or a fingerprint sensor. In addition, on the basis of the batch processing target information received from the batch processing controller 310, the sensor module 321 activates only sensors which require acquisition of sensing data in one or more sensors (Sensor #1, Sensor #2, Sensor #n), and can store sensing data acquired from an activated sensor.

The context module 322 of the data module 320 includes a context computing module (Context #1, Context #2, Context #n) which can calculate at least one piece of context data. Such a context computing module (Context #1, Context #2, Context #n) may calculate information like distance, velocity, altitude, calories, number of steps, exercise state recognition, etc. using at least one piece of sensing data acquired from the sensor module 321.

For example, a context computing module calculates context data corresponding to the exercise state recognition of a user, That is, the context computing module calculates the context data which indicates the exercise state of the user determined by comparing the sensing data acquired by an acceleration sensor, a gyro sensor, a magnetic sensor, etc., with a waveform of the characteristic pattern according to each of preset exercise states. That is, information indicating the user's exercise state (walking, running, biking, etc.) may be obtained from patterns of a period of waveform, intensity, vibration, etc. of the sensing data acquired by the sensor. Further, the context computing module calculates the sensing data (e.g., an atmospheric pressure value) acquired by an atmospheric pressure sensor, such as altitude information, which cannot be acquired only by untreated (raw) sensing data, and may calculate the context data which indicates a exercise state, such as mountain climbing, determined according to the change in altitude by other context computing modules which are interworked with the context computing module. Also, on the basis of the batch processing target information received from the batch processing controller 310, the context module 322 activates only context computing modules which require acquisition of context data in one or more context computing modules (Context #1, Context #2, Context #n), and stores context data acquired from an activated computing module.

The batch data trigger module 330 receives the batch processing target information from the batch target processing unit 311, transmits the received batch processing target information to the data module 320 thereby allowing the data module 320 to select and acquire data based on the batch processing target information, and configures batch data including at least one piece of data acquired from the data module 320, and transmits the batch data to the batch data processing unit 312.

The batch data trigger module 330 can identify the received batch processing target information and, according to the acquired data state on the basis of the identified batch processing target information, determine a batch processing mode which sets a proper batch processing period based on the exercise goal service of the application 147.

For example, the batch processing mode includes a basic batch processing mode and a batch processing switching mode. The basic batch processing mode is preset and batch processing may be available in a general situation by at least one of a batch processing period, reaching threshold capacity of a memory, receiving a signal for requesting a batch process, and a transmission capacity and speed between processors. The batch processing switching mode is set by selectively changing a batch processing period and the amount of data for batch processing, in which a batch processing period can be set to be short or gradually become shorter while the amount of data for batch processing can be set to be small or gradually become smaller.

The batch data trigger module 330 identifies the received batch processing target information, and determines a batch processing mode which sets a proper batch processing period based on the exercise goal service of the application 147 according to the batch processing trigger condition included in the identified batch processing target information.

For example, in the case where the switching condition of the batch processing mode is indicated to determine a batch processing mode based on the acquisition state of target data, the context data corresponding to exercise state recognition information like walking, running, and biking may be selected as target data. When the acquisition of the target data is identified during the process of data acquisition, the batch processing mode is switched to a mode in which batch data is provided in real-time, data which has been acquired and stored so far may be set as batch data, and the set batch data is transmitted to the batch data processing unit 312, while the data acquired thereafter is immediately set as batch data and transmitted to the batch data processing unit 312. Such a process continues until a goal notification of the application for providing the exercise goal service in the application processor 121 is provided.

In another example, in the case where the batch trigger condition indicates that the batch processing mode is to be determined based on the accumulated time according to the acquisition state of the target data, the context data corresponding to exercise state recognition information of walking may be selected as target data. When the acquisition of the target data is identified during the acquisition process of data, a timer may be driven according to the acquisition state of the target data to check the accumulated time. It may be determined whether the accumulated time meets the threshold value defined as the accumulated time which appears when the user continues exercising until the time reaches close to the set goal. Therefore, the batch processing mode is switched to a mode in which batch data is provided in real-time, data which has been acquired and stored so far is set as batch data; and the set batch data is transmitted to the batch data processing unit 312, while the data acquired thereafter is immediately set as batch data and transmitted to the batch data processing unit 312. Such a process continues until a goal notification of the application for providing the exercise goal service in the application processor 121 is provided.

In another example, in the case where the batch processing trigger condition indicates that the batch processing mode is to be determined based on the amount of accumulated data according to the acquisition state of the target data, batch processing can be performed by switching the batch processing mode using substantially the same scheme applied in the batch processing trigger condition using the accumulated time except for the change from the accumulated time to the amount of accumulated data.

In another example, in the case where the batch processing trigger condition indicates that the batch processing mode is to be determined based on the number of pieces of accumulated batch data according to the acquisition state of the target data, batch processing is performed by determining the switching time of a batch processing mode without regard to the acquisition state of after identifying the acquisition of target data.

The batch processing trigger condition determines a batch processing mode using a piece of target data, but the present disclosure is not limited thereto and a batch processing mode can be determined using multiple pieces of target data. For example, if the exercise goal of the application 147 is set to provide a goal notification service regarding exercise distance when the exercise condition is not limited to one and involves walking and running performed together, the context data corresponding to the exercise state recognition information of walking and the context data corresponding to the exercise state recognition information of running both can be selected as target data, and it is preferable that the accumulated time or the threshold value of the amount of accumulated data according to the acquisition state of two such pieces of the target data are set to be different from each other. This is to accurately determine the switching time of a batch processing mode even when the two exercises are performed together, because the range of change in exercise distance by running and the range of change in exercise distance by walking are different from each other.

Figure 4:
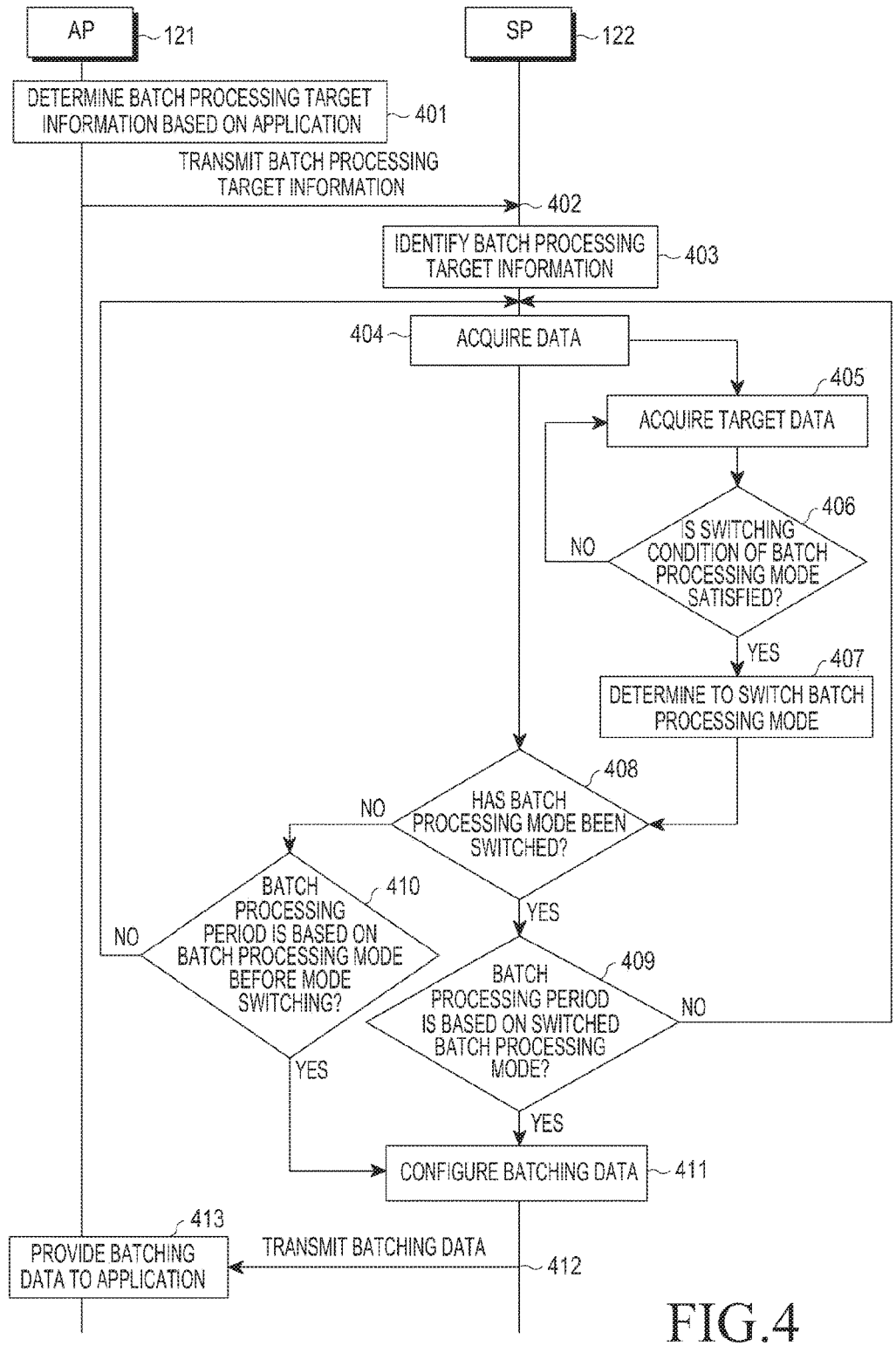
FIG. 4 is a flowchart illustrating an operation of batch processing of data, according to an embodiment of the present disclosure.

FIG. 4 is a flow chart illustrating an step of batch processing of data, according to an embodiment of the present disclosure.

Referring to FIG. 4, in step 401, an application processor 121 determines batch processing target information according to one or more applications 147. The batch processing target information is information about data required for batch processing of the application 147 and includes at least one of a type of data to be batch-processed, a type of target data required for determining a batch processing mode, and a batch processing trigger condition for determining the batch processing mode according to the acquisition state of the target data. The batch processing target information is determined on the basis of at least one exercise goal (e.g., exercise time, exercise distance, type of exercise, calories to burn, number of steps, exercise pace etc.) determined by a user's selection in exercise goal services provided by the one or more applications 147.

For example, the batch processing target information includes sensing data collected by at least one sensor required for performing an operation of the application 147 and/or context data calculated using the sensing data. Further, in the context data, particular data required for determining a proper batch processing period for providing the exercise goal service of the application 147 can be selected as target data. The sensing data and context data is acquired by the supplementary processor. In addition, the context data is information which is calculated using at least one piece of sensing data acquired by a sensor and includes distance, velocity, altitude, calories, number of steps, exercise state recognition, etc. For example, context data corresponding to the exercise state recognition of a user may be data which indicates the exercise state of the user determined by comparing the sensing data acquired by an acceleration sensor, a gyro sensor, a magnetic sensor, etc., with a waveform of the characteristic pattern according to each of preset exercise states. That is, information indicating the user's exercise state (walking, running, biking, etc.) may be obtained from patterns of a period of waveform, intensity, vibration, etc. of the sensing data acquired by the sensor. Further, the context data may be information which can be acquired through a simple operation of the sensing data (e.g., an atmospheric pressure value) acquired by an atmospheric pressure sensor, such as altitude information, which cannot be acquired only by untreated (raw) sensing data, and such information may also be utilized for deriving information displaying the exercise state such as mountain climbing according to the change in altitude.

In addition, the target data is information which has been selected for particular context data required for determining a proper batch processing period for providing the exercise goal service of the application 147. For example, the target data includes the context data corresponding to exercise state recognition information which informs of the user's exercise state, such as walking, running, biking, the number of steps which is used for calculating the distance or consumed calories according to exercise, and altitude information which informs the change in altitude according to an exercise like mountain climbing.

Further, the batch processing trigger condition relates to a condition which enables the determination of a batch processing mode for setting a proper batch processing period for providing the exercise goal service of the application 147. The batch processing trigger condition is information which indicates that the batch processing mode is to be determined according to the acquisition state of the target data. For example, the batch processing trigger condition indicates that the batch processing mode is to be determined by the acquisition state of the target data. If the exercise goal of the application 147 is set to provide a notification service when a particular exercise starts, the context data corresponding to exercise state recognition information, such as walking, running, and biking, can be selected as target data, and when such acquisition of the target data is identified, it can be immediately recognized that the user has started the exercise corresponding to the target data, and thus the batch processing trigger condition indicates to switch the batch processing mode. For example, batch processing is performed in a batch processing mode having a default setting until the target data is acquired, and when the target data has been acquired, the batch processing trigger condition indicates to switch a batch processing mode and allows for batch processing in the switched batch processing mode.

In another example, the batch processing trigger condition indicates that the batch processing mode is to be determined based on the accumulated time according to the acquisition state of the target data. In the case where the exercise goal of the application 147 sets goal values of predetermined time, distance, number of steps, and calories to burn after beginning an exercise, such as walking, and is set to provide a notification service when the corresponding goal is achieved, the context data corresponding to exercise state recognition information of walking may be selected as target data. A timer is driven according to such an acquisition state of the target data to check the accumulated time, and the batch processing trigger condition indicates to switch the batch processing mode by determining whether the accumulated time meets the threshold value defined as the accumulated time which appears when the user continues exercising until the time reaches close to the set goal. For example, batch processing is performed in a batch processing mode having a default setting until the accumulated time reaches to a threshold value, and when the accumulated time has reached a threshold value, the batch processing trigger condition indicates to switch the batch processing mode and allows batch processing in the switched batch processing mode.

In another example, the batch processing trigger condition indicates that the batch processing mode is to be determined based on the amount of accumulated data according to the acquisition state of the target data. In this case, the batch processing trigger condition indicates to switch the batch processing mode by using substantially the same scheme applied in the batch processing trigger condition using the accumulated time except for a change from the accumulated time to the amount of accumulated data. In another example, the batch processing trigger condition indicates that the batch processing mode is determined based on the number of pieces of accumulated batch data according to batch processing of acquired data. In this case, the batch processing trigger condition indicates to switch the batch processing mode by determining the time to switch a batch processing mode, after identifying the acquisition of target data, using the change in number of batch-processed times without regard to the acquisition state of target data.

Additionally, the batch processing trigger condition can determine a batch processing mode using a piece of target data, but the present disclosure is not limited thereto and a batch processing mode can be determined using multiple pieces of target data. For example, if the exercise goal of the application 147 is set to provide a goal notification service regarding exercise distance, when the exercise condition is not limited to one, and involves walking and running performed together, the context data corresponding to the exercise state recognition information of walking and the context data corresponding to the exercise state recognition information of running both can be selected as target data, and it is preferable that the accumulated time or the threshold value of the amount of accumulated data according to the acquisition state of two such pieces of the target data are set to be different from each other. This is to accurately determine the switching time of a batch processing mode even when the two exercises are performed together, because the range of change in exercise distance by running and the range of change in exercise distance by walking are different from each other.

In step 402, an application processor 121 transmits the determined batch processing target information to a supplementary processor 122. The application processor 121 requests batch data to be batch-processed in a batch processing mode according to the state of data to be acquired by the supplementary processor 122 based on the batch processing target information.

In step 403, a supplementary processor 122 receives and identifies the batch processing target information. The supplementary processor 122 identifies a type of data required for batch processing included in the batch processing target information In addition the supplementary processor 122 identifies a batch processing trigger condition included in the batch processing target information, and determines a switching condition of a batch processing mode according to the identified batch processing trigger condition. In operation 404, the supplementary processor 122 selects and acquires data corresponding to the type of data included in the batch processing target information identified in operation 403. For example, the supplementary processor 122 activates, on the basis of the batch processing target information, only sensors which require acquisition of sensing data in one or more sensors provided in an electronic device 101 and stores sensing data acquired from an activated sensor. In addition, when a type of data includes context data, the supplementary processor 122 performs an arithmetic operation for calculating the corresponding context data and calculates the context data using sensing data required for calculating the context data. The supplementary processor 122 further selects and stores target data required for determining the batch processing mode in the context data.

In step 405, the supplementary processor 122 acquires target data according to a batch processing trigger condition included in the batch processing target information.

In step 406, the supplementary processor 122 determines whether the acquisition state of the target data satisfies the switching condition of a batch processing mode determined in step 404 according to the batch processing trigger condition. The supplementary processor 122 determines whether a batch processing mode has been switched by determining whether the acquisition state of the target data satisfies the switching condition of the batch processing mode. For example, in the case where the switching condition of the batch processing mode indicates to switch the batch processing mode based on the acquisition state of target data, the target data may be context data corresponding to exercise state recognition information, such as walking and running. When the acquisition of such target data is identified, it is determined that the switching condition of the batch processing mode is satisfied, and the batch processing mode is switched. As another example, in the case where the switching condition of the batch processing mode indicates to switch the batch processing mode based on the accumulated time according to the acquisition state of the target data, the target data may be context data corresponding to the exercise state recognition information of walking. A timer is driven according to such acquisition state of the target data to check the accumulated time, and the switching condition of the batch processing mode indicates to switch the batch processing mode by determining that the switching condition of the batch processing mode is satisfied.

In step 407, when the acquisition state of the target data satisfies the switching condition of the batch processing mode the supplementary processor 122, the supplementary processor 122 determines to switch the batch processing mode. When the batch processing mode is determined to switch, the supplementary processor 122 indicates to change the batch processing mode to a batch processing switching mode, and selectively modifies and sets a batch processing period and/or the amount of data for batch processing of the batch processing switching mode. The supplementary processor 122 sets the batch processing switching mode based on the batch processing target information identified in step 403. For example, the batch processing mode includes a basic batch processing mode and a batch processing switching mode. The basic batch processing mode is to perform batch processing by at least one of a batch processing period, reaching threshold capacity of a memory, receiving a signal for requesting a batch process, and a transmission capacity and speed between processors. The batch processing switching mode is to perform batch processing by selectively modifying and setting a batch processing period and/or an amount of data for batch processing. For example, a batch processing period can be set to be short or to become gradually shorter relative to the number of batch processing times, while the amount of data for batch processing can be set to be small or to become gradually smaller relative to the number of batch processing times, by using the setting of the batch processing switching mode.

In step 408, when data is acquired in step 404, the supplementary processor 122 determines whether the batch processing mode is switched according to the presence/absence of an indication to switch the batch processing mode in step 407 after a switching condition of the batch processing mode is satisfied in step 406. That is, after data is acquired in step 404, when the target data is not acquired in step 404 or when a switching condition of a batch processing mode is not satisfied in step 406, it can be determined that a batch processing mode is not switched. On the contrary, after data is acquired in step 404, when a switching condition of a batch processing mode is satisfied in step 406 and the batch processing mode is indicated to switch in step 407, it can be determined that a batch processing mode is switched.

In step 409, when it is determined that the batch processing mode has been switched to the batch processing switching mode in step 408, the supplementary processor 122 stores the acquired data according to the batch processing switching mode and determines whether a batch processing period according to the batch processing switching mode is satisfied.

In step 410, when it is determined that the batch processing mode has not been switched in step 408, the supplementary processor 122 stores the acquired data according to the basic batch processing mode and determines whether a batch processing period according to the basic batch processing mode is satisfied.

When the batch processing period according to steps 409 or 410 is not satisfied, the supplementary processor 122 returns to step 404 to continue acquiring data.

In step 411, when the batch processing period according to steps 409 and 410 is satisfied, the supplementary processor 122 sets the stored data as batch data.

In step 412, the supplementary processor 122 transmits batch data set in step 411 to the application processor 121.

In step 413, the application processor 121 provides the received batch data to one or more applications 147. At this time, the batch data can be batch-processed on the application processor 121 in a batch processing period according to the batch processing mode in the supplementary processor 122. For example, in the case where batch processing of batch data is performed in the basic batch processing mode, batch data is provided to the application 147 in every preset batch processing period. When batch processing of batch data is performed in the batch processing switching mode and the batch processing switching mode is set to have a batch processing period set in real-time, the batch data is provided to the application 147 in real-time. Accordingly, the application 147 can provide an exercise goal service provides a notification to a user when the user achieves a preset exercise goal. Further, when a goal notification by the exercise goal service of the application 147 is provided, the application processor 121 indicates a switch of the batch processing mode to the supplementary processor 122. The switch of the batch processing mode can be indicated to be either switched back to a basic batch processing mode or switched to a batch processing switching mode in which a modified batch processing period or modified amount of data for batch processing is set.

Figure 5:
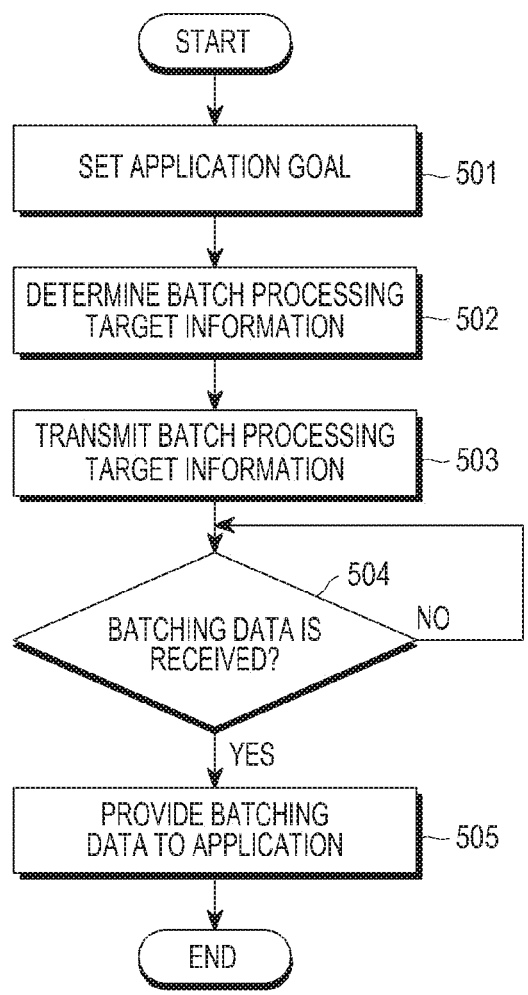
FIG. 5 is a flowchart illustrating an operation of batch processing data by an application processor, according to an embodiment of the present disclosure.

FIG. 5 is a flowchart illustrating an operation of batch processing data by an application processor, according to an embodiment of the present disclosure.

Referring to FIG. 5. step 501, an application processor 121 receives, from one or more applications 147, goal information about at least one of exercise time, exercise distance, number of steps, calories to burn, and exercise state recognition, which are set by a user of the application 147.

In step 502, the application processor 121 determines batch processing target information according to goal information of the one or more applications 147. The batch processing target information is information about data required for batch processing of the application 147, and includes at least one of a type of data to be batch-processed, a type of target data required for determining a batch processing mode, and a batch processing trigger condition for determining the batch processing mode according to the acquisition state of the target data.

In step 503, the application processor 121 transmits the determined batch processing target information to a supplementary processor 122. The application processor 121 requests batch data to be batch-processed in a batch processing mode according to the state of data to be acquired by the supplementary processor 122 based on the batch processing target information.

In step 504, the application processor 121 receives batch data from the supplementary processor 122. The application processor 121 can be driven either in a sleep mode or in an operating mode. For example, the application processor 121 can be driven in sleep mode during the time when batch data is not received from the supplementary processor 122, and the sleep mode can be switched to an operation mode to drive the application processor 121 when batch data is received from the supplementary processor 122.

When batch data is received from the supplementary processor 122 in step 504, the application processor 121 provides the received batch data to one or more applications 147 in step 505. The application processor 121 rearranges batch data received from the supplementary processor 122 according to the type of data required for the one or more applications 147, and provides the rearranged data to each of the one or more applications 147. The batch data is batch-processed by the application processor 121 in a different batch processing period according to a batch processing mode in the supplementary processor 122. For example, when batch processing of batch data is performed in the basic batch processing mode, the application processor 121 receives batch data in preset batch periods and provides the batch data to the application 147. When batch processing of batch data is performed in the batch processing switching mode, the application processor 121 receives batch data in real-time and provides the batch data to the application 147 when the batch processing switching mode is set to have a batch processing period set in real-time.

When batch data is not received from the supplementary processor 122 in step, 504, the application processor 121 continues to wait for batch data to be received.

Accordingly, the application 147 can provide an exercise goal service which provides a notification service to a user for a goal achievement when the user has accomplished a preset exercise goal.

Figure 6:
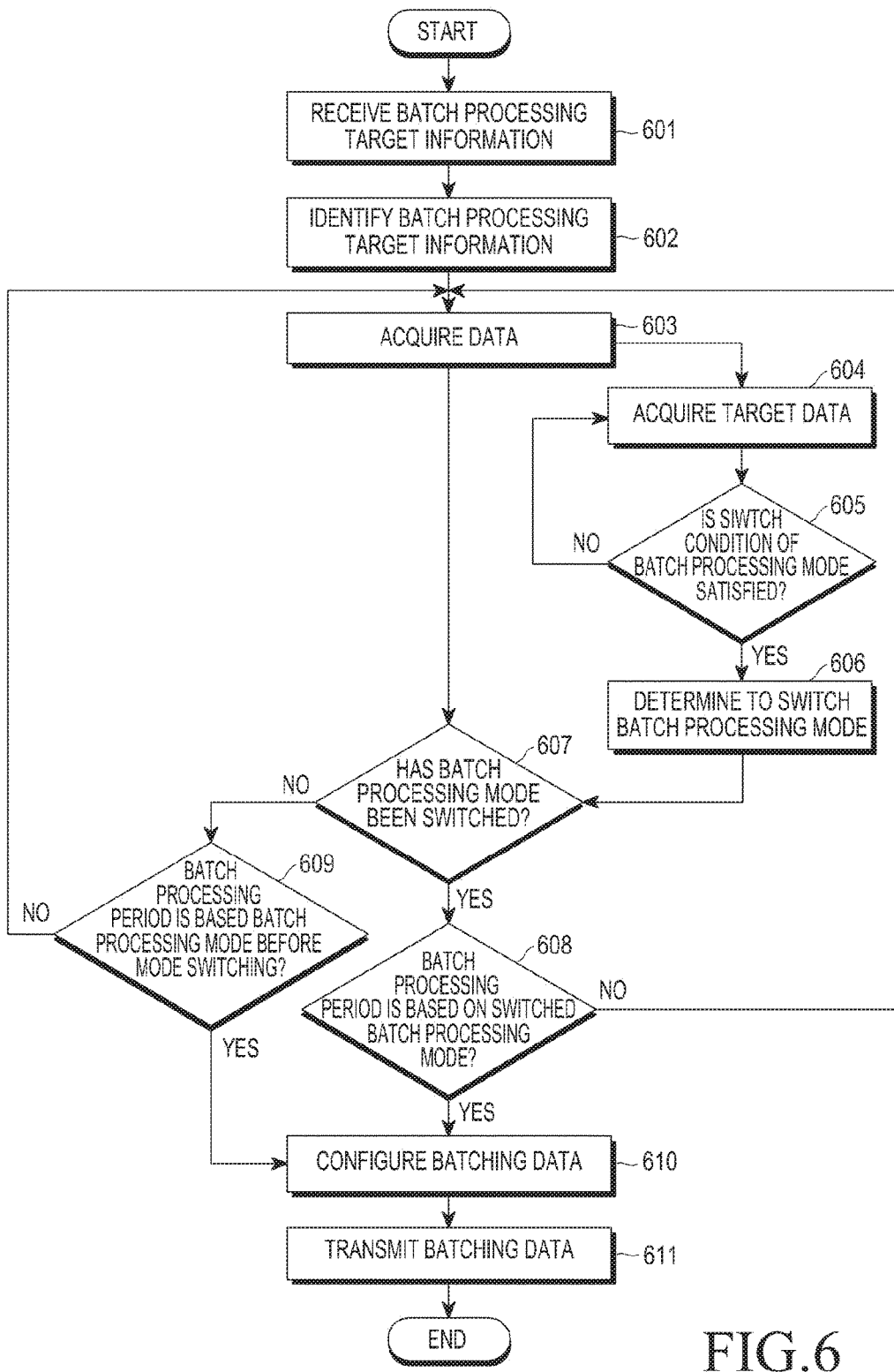
FIG. 6 is a flowchart illustrating an operation of batch processing data by a supplementary processor, according to an embodiment of the present disclosure.
Figure 7:
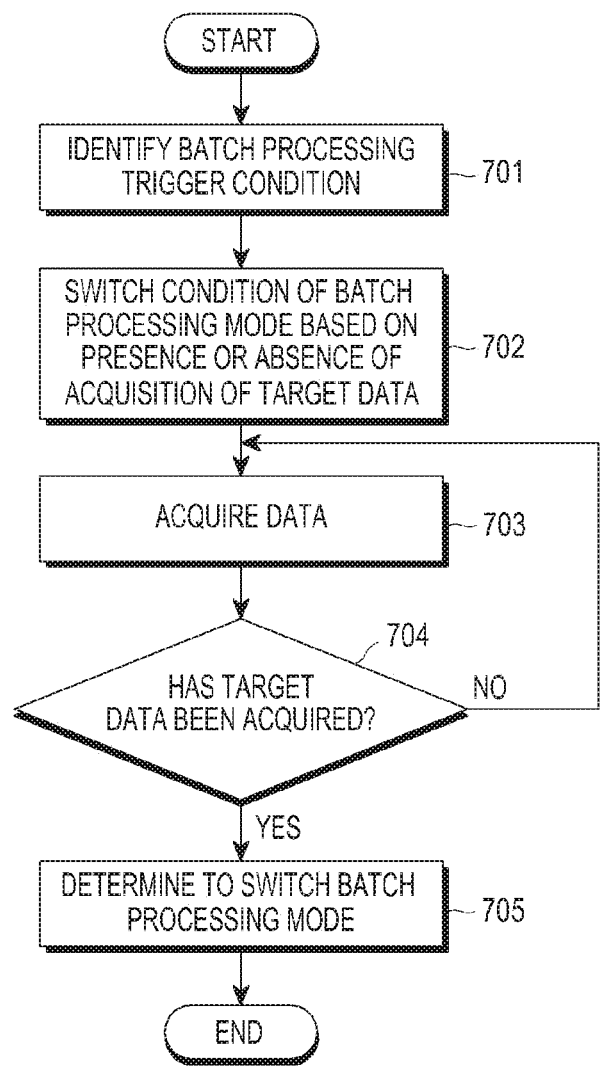
FIG. 7 is a flowchart illustrating a detailed process for determining a batch processing mode by a supplementary processor, according to an embodiment of the present disclosure.
Figure 8:
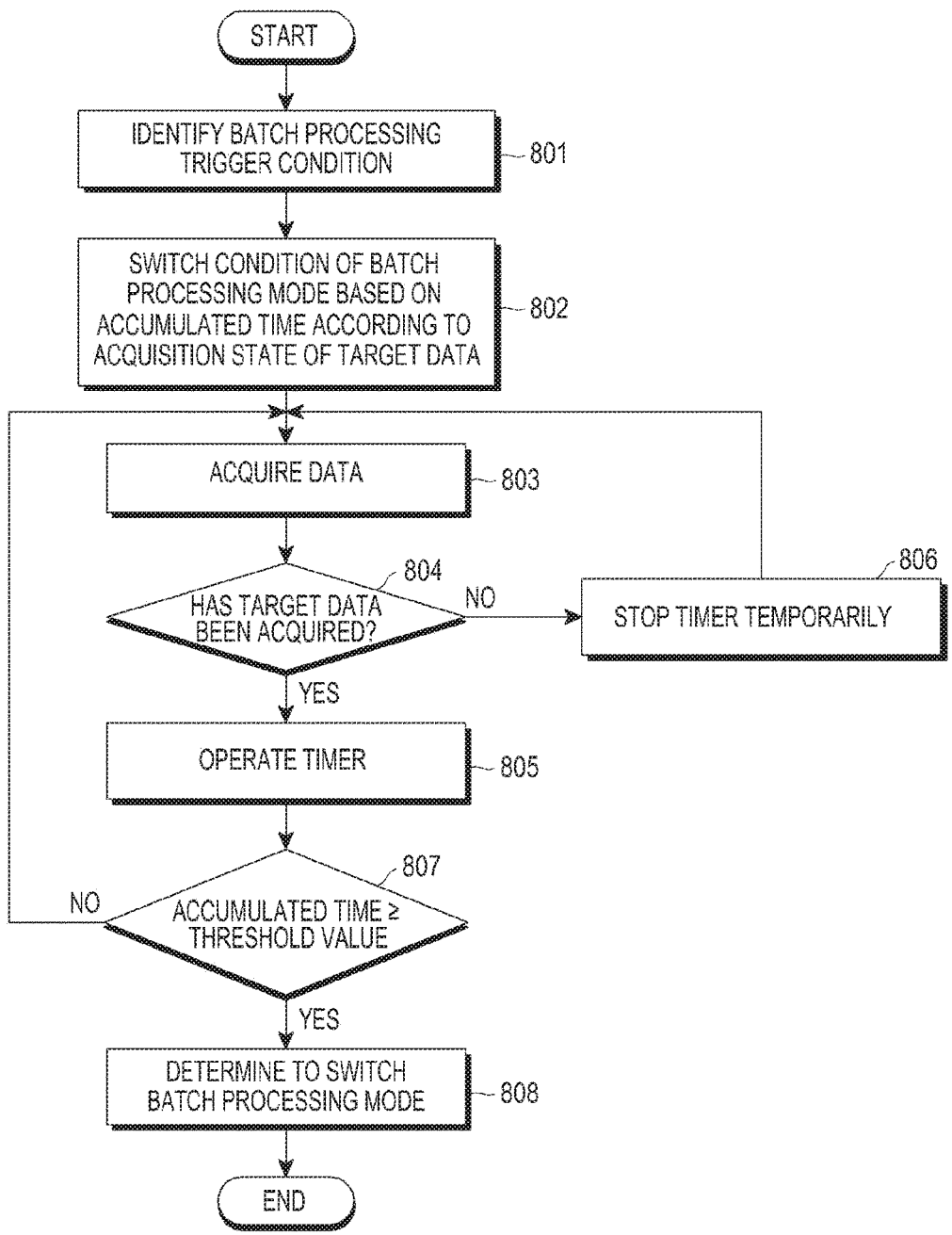
FIG. 8 is a flowchart illustrating a detailed process for determining a batch processing mode by a supplementary processor, according to another embodiment of the present disclosure.

FIG. 6 is a flowchart illustrating an operation of batch processing data by a supplementary processor, according to an embodiment of the present disclosure. FIG. 7 is a flowchart illustrating a detailed process for determining a batch processing mode by a supplementary processor, according to an embodiment of the present disclosure. FIG. 8 is a flowchart illustrating a detailed process for determining a batch processing mode by a supplementary processor, according to another embodiment of the present disclosure.

Referring to FIG. 6, in step 601, a supplementary processor 122 receives batch processing target information from an application processor 121.

In step 602, the supplementary processor 122 identifies the received batch processing target information. The supplementary processor 122 identifies the type of data required for batch processing included in the batch processing target information. In addition, the supplementary processor 122 identifies batch processing trigger condition included in the batch processing target information, and determines a switching condition of a batch processing mode according to identified batch processing trigger condition.

In step 603, the supplementary processor 122 selects and acquires data corresponding to the type of data included in the batch processing target information identified in step 602. For example, on the basis of the batch processing target information, the supplementary processor 122 activates only sensors which require acquisition of sensing data in one or more sensors provided in an electronic device 101, and stores sensing data acquired from an activated sensor. In addition, when the type of data includes context data, a supplementary processor 122 performs an arithmetic operation for calculating the corresponding context data and calculates context data using sensing data required for calculating context data. The supplementary processor 122 further selects and stores target data required for determining the batch processing mode in the context data.

In step 604, the supplementary processor 122 acquires target data according to a batch processing trigger condition included in the batch processing target information.

In step 605, the supplementary processor 122 determines whether the acquisition state of the target data satisfies the switching condition of the batch processing mode determined in step 602, according to the batch processing trigger condition. The supplementary processor 122 determines whether the acquisition state of the target data satisfies the switching condition of the batch processing mode and determines whether the batch processing mode has been switched. For example, in a case where the switching condition of the batch processing mode indicates to switch the batch processing mode based on the acquisition state of target data, the target data may be context data corresponding to exercise state recognition information, such as walking and running. When the acquisition of such target data is identified, it is determined that the switching condition of the batch processing mode is satisfied, and the batch processing mode indicates to switch. For another example, in a case where the switching condition of the batch processing mode is indicated to switch the batch processing mode based on the accumulated time according to the acquisition state of the target data, the target data may be context data corresponding to the exercise state recognition information of walking. A timer is driven according to such acquisition state of the target data to check the accumulated time, and the switching condition of the batch processing mode indicates to switch the batch processing mode by determining that the switching condition of the batch processing mode is satisfied.

In step 606, when the acquisition state of the target data satisfies the switching condition of the batch processing mode the supplementary processor 122 determines to switch the batch processing mode. When the batch processing mode is determined to switch, the supplementary processor 122 indicates to change the batch processing mode to a batch processing switching mode, and selectively modifies and sets a batch processing period and/or the amount of data for batch processing of the batch processing switching mode. The supplementary processor 122 sets the batch processing switching mode based on the batch processing target information identified in step 602. For example, the batch processing mode includes a basic batch processing mode and a batch processing switching mode. The basic batch processing mode is to perform batch processing by at least one of a batch processing period, reaching threshold capacity of a memory, receiving a signal for requesting a batch process, and a transmission capacity and speed between processors. The batch processing switching mode is to perform batch processing by selectively modifying and setting a batch processing period and/or an amount of data for batch processing. For example, a batch processing period can be set to be short or to become gradually shorter relative to the number of batch processing times, while the amount of data for batch processing can be set to be small or to become gradually smaller relative to the number of batch processing times, by using the setting of the batch processing switching mode.

In step 607, when data is acquired in step 603, the supplementary processor 122 determines whether the batch processing mode is switched according to the presence/absence of an indication to switch the batch processing mode in step 606 after a switching condition of the batch processing mode is satisfied in step 605. That is, after data is acquired in step 603, when the target data is not acquired in step 603 or when a switching condition of a batch processing mode is not satisfied in step 605, it can be determined that a batch processing mode is not switched. On the contrary, after data is acquired in step 603, when a switching condition of a batch processing mode is satisfied in step 605 and the batch processing mode is indicated to switch in step 606, it can be determined that a batch processing mode is switched.

In step 608, when it is determined that the batch processing mode has been switched to the batch processing switching mode in step 607, the supplementary processor 122 stores the acquired data according to the batch processing switching mode and determines whether a batch processing period according to the batch processing switching mode is satisfied.

In step 609, when it is determined that the batch processing mode has not been switched in step 607, the supplementary processor 122 stores the acquired data according to the basic batch processing mode and determines whether a batch processing period according to the basic batch processing mode is satisfied.

When the batch processing period according to steps 608 or 609 is not satisfied, the supplementary processor 122 returns to step 603 to continue acquiring data.

In step 610, when the batch processing period according to steps 608 and 609 is satisfied, the supplementary processor 122 sets the stored data as batch data.

In step 611, the supplementary processor 122 transmits batch data set in step 640 to the application processor 121.

Referring to FIG. 7, the process for determining the batch processing mode in details provided.

In step 701, the supplementary processor 122 identifies a batch processing trigger condition included in the batch processing target information.

In step 702, the supplementary processor 122 determines the switching condition of the batch processing mode according to the identified batch processing trigger condition, and context data corresponding to exercise state recognition information, such as walking, running, and biking, can be selected for the target data when the switching condition of the batch processing indicates to switch the batch processing mode based on the acquisition state of target data.

In step 703, the supplementary processor 122 selects and acquires data corresponding to the type of data included in the received batch processing target information.

In step 704, the supplementary processor 122 identifies whether target data is acquired in the data acquired in step 703 When the acquisition of the target data is identified, it is determined that the switching condition of the batch processing mode is satisfied and thus supplementary processor 122 indicates to switch the batch processing mode.

In step 705, when the acquisition state of the target data satisfies the switching condition of the batch processing mode, the supplementary processor 122 determines to switch the batch processing mode.

Referring to FIG. 8, another example of an operation for determining the batch processing mode is provided.

In step 801, the supplementary processor 122 identifies the batch processing trigger condition included in the batch processing target information.

In step 802, the supplementary processor 122 determines the switching condition of the batch processing mode according to the identified batch processing trigger condition, and context data corresponding to exercise state recognition information of walking can be selected as the target data when the switching condition of the batch processing mode indicates to switch the batch processing mode based on an accumulated time according to the acquisition state of target data.

In step 803, the supplementary processor 122 selects and acquires data corresponding to the type of data included in the received batch processing target information.

In step 804, the supplementary processor 122 identifies whether target data is acquired in the data acquired in step 803.

In step 805, when the acquisition of the target data is identified, the supplementary processor 122 drives a timer, thereby identifying the accumulated time according to the acquisition of the target data.

On the other hand, in step 806, when the acquisition of the target data is not identified, the supplementary processor 122 temporarily stops the operation of the timer.

In step 807, when the accumulated time according to the acquisition state of the target data reaches a threshold value identified in the switching condition of the batch processing mode, the supplementary processor 122 determines that the switching condition of the batch processing mode is satisfied, thereby indicating to switch the batch processing mode. The threshold value may be a definition of the accumulated time which appears when a user continues exercising until the time reaches close to the set goal.

In step 808, when the accumulated time according to the acquisition of the target data reaches to the threshold value defined in the switching condition of the batch processing mode, the supplementary processor 122 determines to switch the batch processing mode.

When the accumulated time does not reach the threshold value, the supplementary processor 122 returns to step 803.

As another example of an operation for determining the batch processing mode, when the switching condition of the batch processing mode is either a condition for indicating to switch a batch processing mode based on the amount of the accumulated data according to the acquisition state of the target data or a condition for indicating to switch the batch processing mode based on the number of pieces of accumulated batch data according to batch processing of acquired data, the batch processing mode is determined by substantially the same operation as the operation illustrated in FIG. 8 in which the accumulated time is substituted by the amount of accumulated data or the number of pieces of accumulated batch data.

Figure 9:
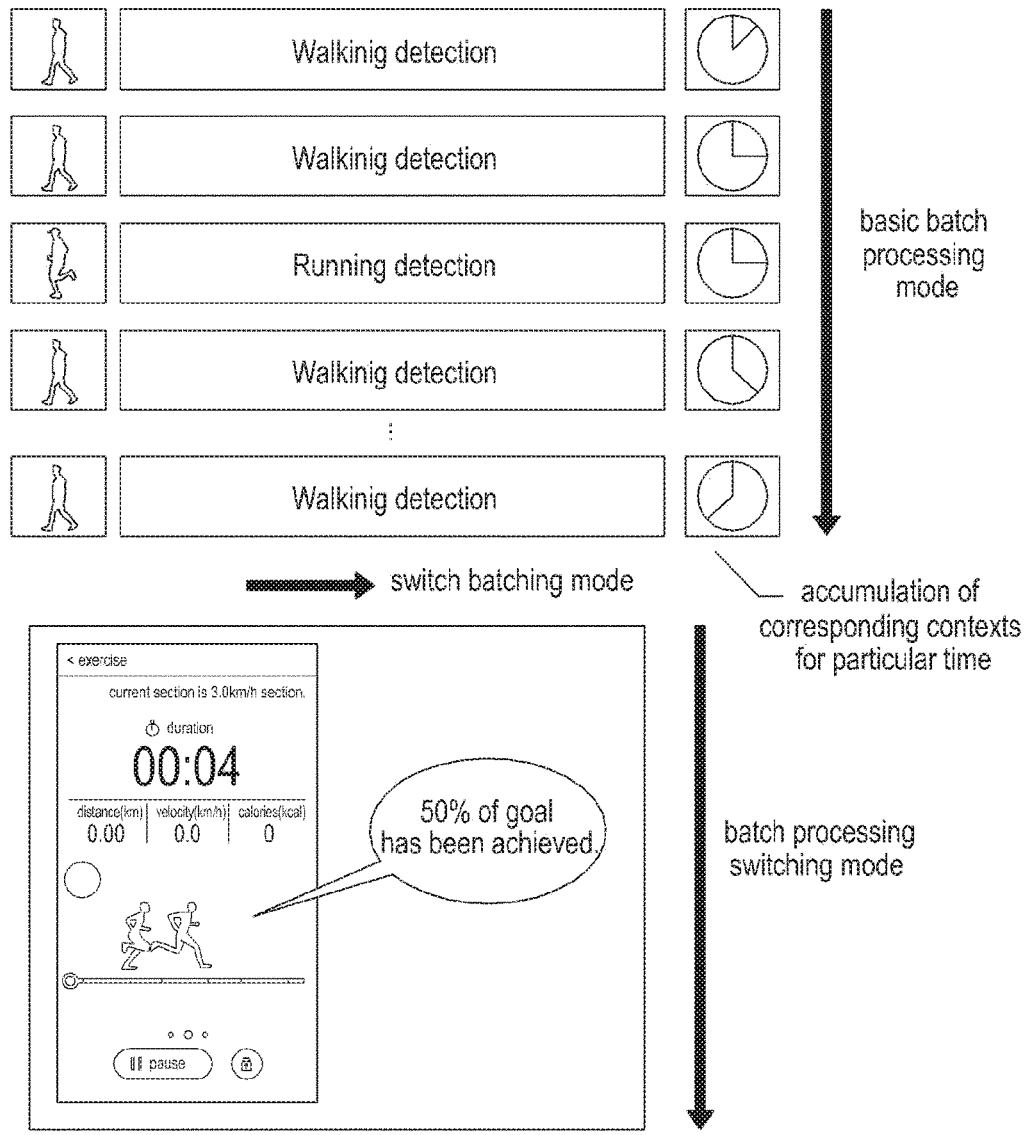
FIG. 9 illustrates a method for determining a batch processing mode through accumulated time, according to an embodiment of the present disclosure.

FIG. 9 illustrates a method for determining a batch processing mode through accumulated time, according to an embodiment of the present disclosure.

Referring to FIG. 9, in a method for determining a batch processing mode by accumulated time, when an exercise goal of an application 147 sets goal values of a predetermined time, distance, number of steps, and/or calories to burn (e.g., walking for 30 minutes, walking 3 km, walking 300 steps, or burning 3000 calories) after beginning an exercise, such as walking, and the application 147 is set to provide a notification service when the corresponding goal is achieved, context data corresponding to exercise state recognition information of walking can be selected as target data. In addition, when a threshold value corresponding to the accumulated time based on the acquisition state of the target data according to the goal values is determined, a timer is driven, thereby identifying the accumulated time. For example, when context data corresponding to walking is acquired, time accumulation is performed. When context data corresponding to running is subsequently acquired, the time accumulation stops. Then when the context data corresponding to walking is acquired again, the time accumulation is resumed. Therefore, when the total accumulated time reaches a threshold value based on the goal value, the batch processing mode is switched to a mode in which batch data can be provided in real-time.

The above embodiment of the present disclosure provides for a case in which one target exercise state and one goal corresponding thereto are assigned. However, in another embodiment, multiple target exercise states and goals (e.g., walking for 30 minutes and running for 10 minutes) corresponding thereto may be set. In this case, when a goal corresponding to any one of exercise states in the multiple exercise states and goals is accomplished, the batch processing mode is switched to the batch processing switching mode in which batch data can be provided in real-time. For example, when any one of goals in the multiple preset exercise states and goals (e.g., walking for 30 minutes and running for 10 minutes) is accomplished, the batch processing mode is switched to a batch processing switching mode in which batch data can be provided in real-time.

Figure 10:
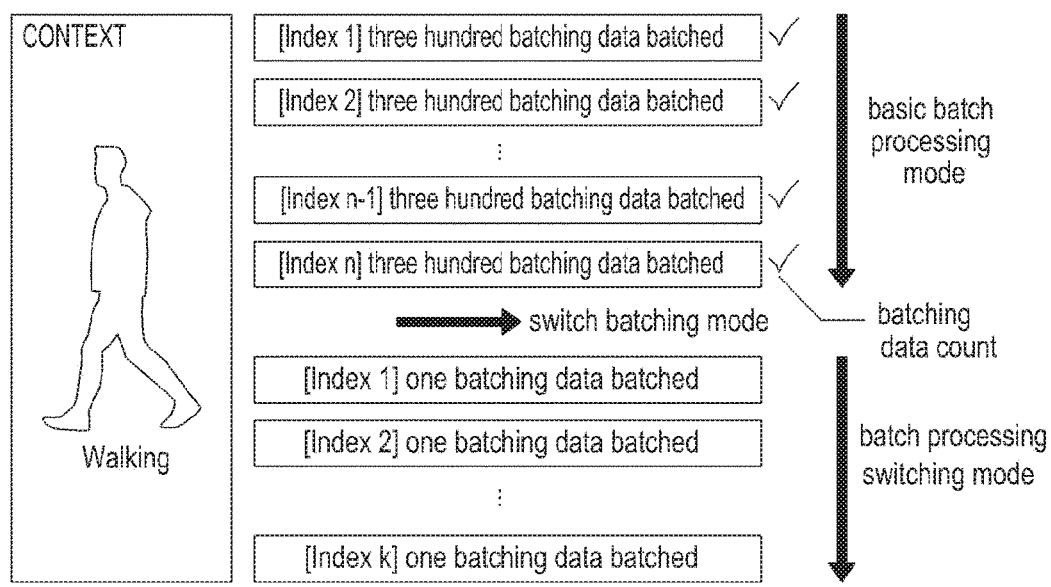
FIG. 10 illustrates a method for determining a batch processing mode through an amount of accumulated data, according to an embodiment of the present disclosure.

FIG. 10 illustrates a method for determining a batch processing mode through an amount of accumulated data, according to an embodiment of the present disclosure.

Referring to FIG. 10, in a method for determining a batch processing mode by accumulated data, when an exercise goal of an application 147 sets goal values of a predetermined time, distance, number of steps, and/or calories to burn (e.g., walking for 30 minutes, walking 3 km, walking 300 steps, or burning 3000 calories) after beginning an exercise, such as walking, and the application 147 is set to provide a notification service when the corresponding goal is achieved, context data corresponding to exercise state recognition information of walking can be selected as target data. The selected target data is accumulated stack by a predetermined number to be batch-processed. In addition, when a threshold value corresponding to the number of stacks based on the acquisition state of the target data according to the goal values is determined, the number of stacks is counted whenever the target data is stacked. When the number of counted stacks reaches a threshold value according to the goal values, the batch processing mode is switched to a batch processing switching mode in which batch data can be provided in real-time.

Figure 11:
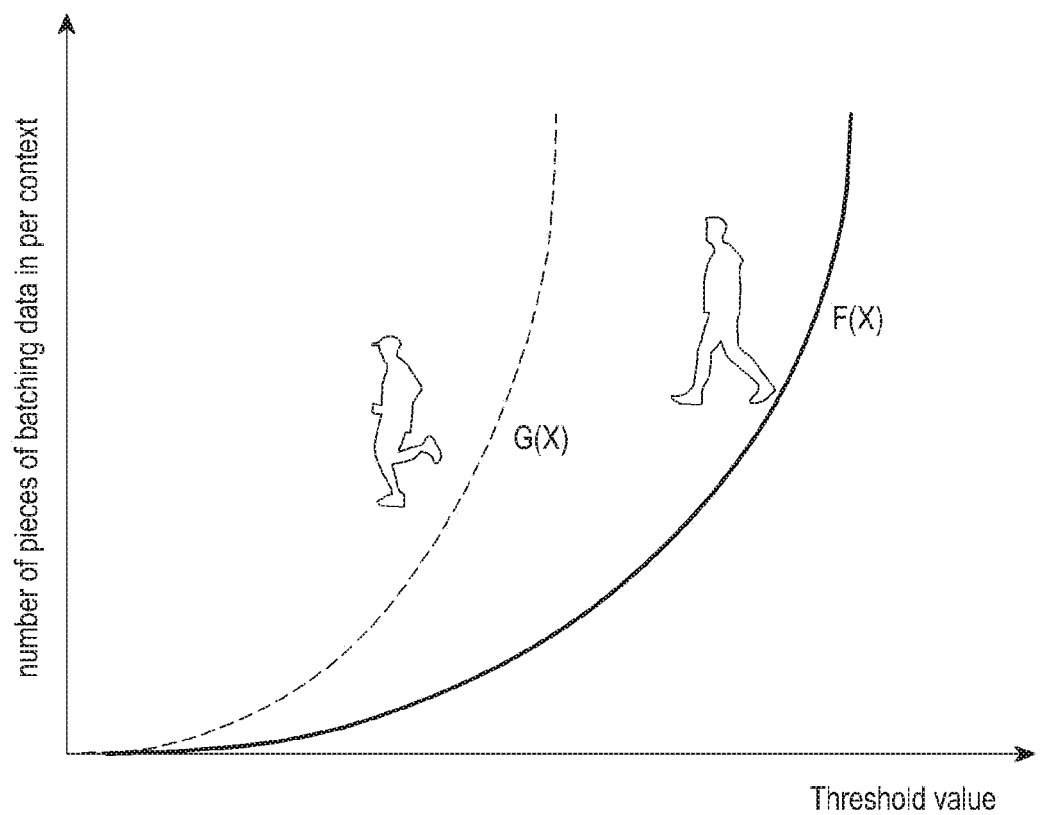
FIG. 11 is a graph illustrating a relationship between acquired data, according to an embodiment of the present disclosure.

FIG. 11 is a graph illustrating a relationship between acquired data, according to an embodiment of the present disclosure.

Referring to FIG. 11, a batch processing trigger condition determines a batch processing mode using multiple pieces of target data. That is, threshold value of amount of accumulated data according to an acquisition state of each of the target data are set to be different from each other. For example, F(X) shown on the graph represents relationship of threshold value according to number of pieces of batching data of context data corresponding to exercise state recognition information of walking, and G(X) on the graph represents relationship of threshold value according to number of pieces of batching data of context data corresponding to exercise state recognition information of running. Accordingly, the difference between the range of change in an exercise distance by running and the range of change in exercise distance by walking is compensated by setting a reference of comparison with a threshold value according to number of pieces of batching data of two types of context data, and thus the switching time of the batch processing mode can be more accurately determined.

Figure 12:
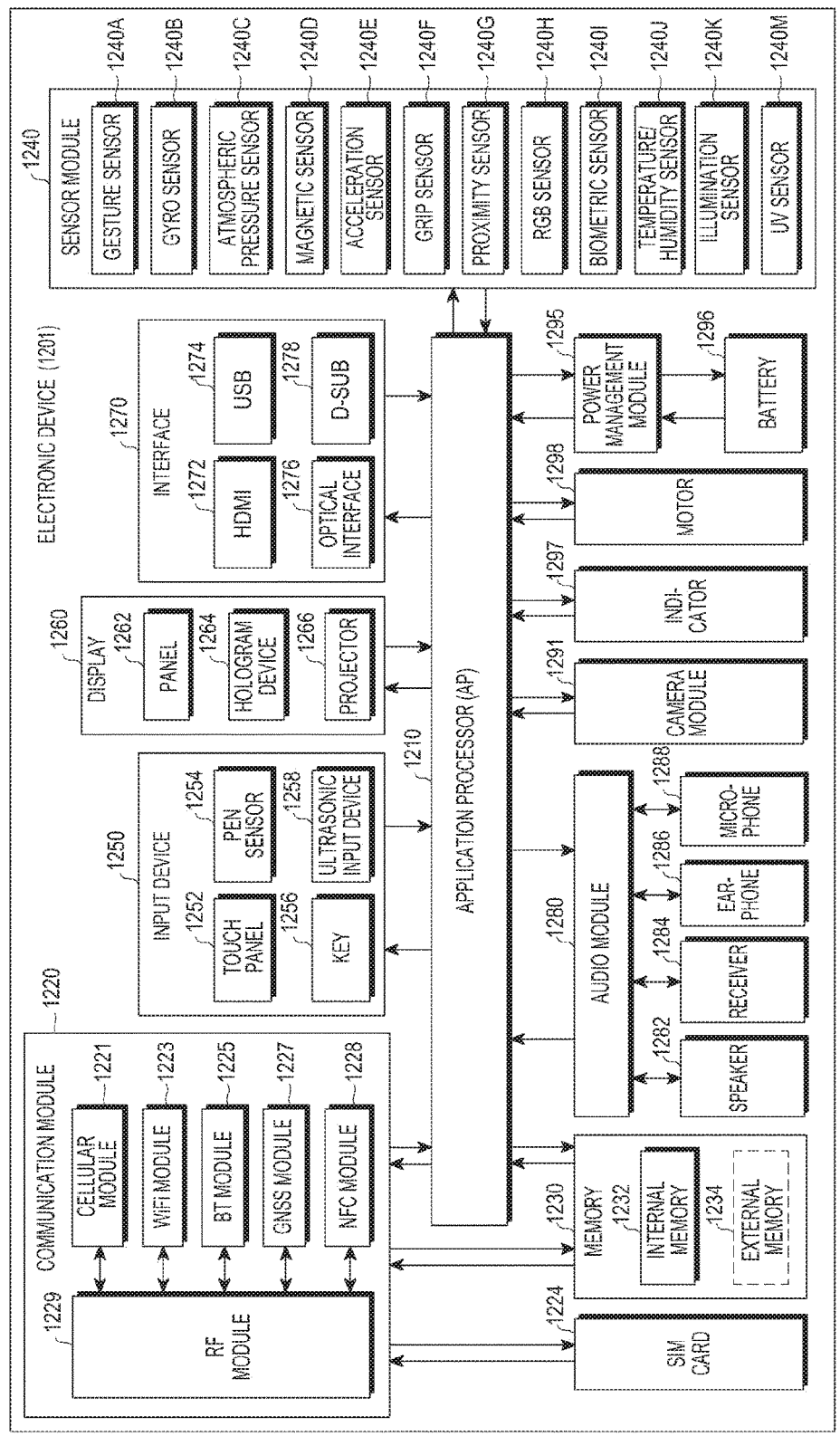
FIG. 12 is a block diagram illustrating an electronic device, according to an embodiment of the present disclosure.

FIG. 12 is a block diagram illustrating an electronic device, according to embodiment of the present disclosure.

Referring to FIG. 12, an electronic device 1201 is provided. The electronic device 1201 may include all or some of the electronic device 101 illustrated in FIG. 1. The electronic device 1201 includes at least one Application Processor (AP) 1210, a communication module 1220, a Subscriber Identification Module (SIM) card 1224, a memory 1230, a sensor module 1240, an input device 1250, a display 1260, an interface 1270, an audio module 1280, a camera module 1291, a power management module 1295, a battery 1296, an indicator 1297, and a motor 1298.

The AP 1210 controls a plurality of hardware or software components connected thereto by driving an operating system or an application program and performs a variety of data processing and calculations. The AP 1210 may be embodied as a System on Chip (SoC). The processor 1210 may further include a Graphic Processing Unit (GPU) and/or an image signal processor. The AP 1210 may also include at least some (for example, a cellular module 1221) of the components illustrated in FIG. 12. The processor 1210 loads, into a volatile memory, instructions or data received from at least one (e.g., a non-volatile memory) of the other elements, processes the loaded instructions or data, and stores various data in a non-volatile memory.

The communication module 1220 may have a configuration equal or similar to the communication interface 170 of FIG. 1. The communication module 1220 includes the cellular module 1221, a Wi-Fi module 1223, a BT module 1225, a GNSS module 1227, an NFC module 1228, and a Radio Frequency (RF) module 1229.

The cellular module 1221 provides a voice call, video call, text message services, or Internet services through a communication network. The cellular module 1221 distinguishes between and authenticates electronic device 1201 within a communication network using the SIM card 1224. The cellular module 1221 may perform at least some of the functions which may be provided by the AP 1210. The cellular module 1221 may include a Communication Processor (CP).

The Wi-Fi module 1223, the BT module 1225, the GPS module 1227, and the NFC module 1228 may include a processor for processing data transmitted/received through the corresponding module. At least some of the cellular module 1221, the WiFi module 1223, the BT module 1225, the GNSS module 1227, and the NFC module 1228 may be included in one Integrated Chip (IC) or IC package.

The RF module 1229 transmits and receives a communication signal (for example, an RF signal). The RF module 1229 may include a transceiver, a Power Amp Module (PAM), a frequency filter, a Low Noise Amplifier (LNA), or an antenna. At least one of the cellular module 1221, the WiFi module 1223, the BT module 1225, the GPS module 1227, and the NFC module 1228 may transmit/receive an RF signal through a separate RF module.

The SIM card 1224 may be a card including an embedded SIM, and contains unique identification information (e.g., an Integrated Circuit Card Identifier (ICCID)) or subscriber information (e.g., an International Mobile Subscriber Identity (IMSI)).

The memory 1230 (for example, a memory 130) includes an internal memory 1232 or an external memory 1234.

The internal memory 1232 may include a volatile memory (for example, a Dynamic Random Access Memory (DRAM), a Static RAM (SRAM), a Synchronous Dynamic RAM (SDRAM), and the like) and a non-volatile memory (for example, a One Time Programmable Read Only Memory (OTPROM), a Programmable ROM (PROM), an Erasable and Programmable ROM (EPROM), an Electrically Erasable and Programmable ROM (EEPROM), a flash memory (for example, a NAND flash memory or a NOR flash memory), a hard driver, or a Solid State Drive (SSD).

The external memory 1234 may include a flash drive, for example, a Compact Flash (CF), a Secure Digital (SD), a Micro Secure Digital (Micro-SD), a Mini Secure Digital (Mini-SD), an eXtreme Digital (xD), a memory stick, etc. The external memory 1234 may be functionally and/or physically connected to the electronic device 1201 through various interfaces.

The sensor module 1240 measures a physical quantity or detects an operation state of the electronic device 1201, and converts the measured or detected information to an electrical signal. The sensor module 1240 includes at least one of a gesture sensor 1240A, a gyro sensor 1240B, an atmospheric pressure sensor 1540C, a magnetic sensor 1540D, an acceleration sensor 1540E, a grip sensor 1540F, a proximity sensor 1540G, a color sensor (for example, red, green, and blue (RGB) sensor) 1540H, a biometric sensor 1540I, a temperature/humidity sensor 1240J, an illumination sensor 1240K, and an Ultra Violet (UV) sensor 1540M. Additionally or alternatively, the sensor module 1240 may include an E-nose sensor, an electromyography (EMG) sensor, an electroencephalogram (EEG) sensor, an electrocardiogram (ECG) sensor, an Infrared (IR) sensor, an iris sensor, and/or a fingerprint sensor. The sensor module 1240 may further include a control circuit for controlling at least one sensor included therein. The electronic device 1201 may further include a processor configured to control the sensor module 1240 as a part of or separately from the AP 1210, and may control the sensor module 1240 while the AP 1210 is in a sleep state.

The input device 1250 includes a touch panel 1252, a (digital) pen sensor 1254, a key 1256, or an ultrasonic input device 1258.

The touch panel 1252 may use at least one of a capacitive type, a resistive type, an infrared type, and an ultrasonic type. The touch panel 1252 may further include a control circuit. The touch panel 1252 may further include a tactile layer, and provide a tactile reoperation to a user.

The (digital) pen sensor 1254 may include a recognition sheet which is a part of the touch panel 1252 or a separate recognition sheet.

The key 1256 may include a physical button, an optical key, or a keypad.

The ultrasonic input unit 1258 inputs data through an input means that generates an ultrasonic signal, and the electronic device 1201 identifies data by detecting a sound wave with a microphone 1288.

The display 1260 (for example, the display 160) may include a panel 1262, a hologram device 1264, or a projector 1266. The panel 1262 may include a component equal or similar to the display 160 of FIG. 1. The panel 1262 may be embodied to be, for example, flexible, transparent, or wearable. The panel 1262 may also be configured to be integrated with the touch panel 1252 as a single module.

The hologram device 1264 shows a stereoscopic image in the air by using interference of light.

The projector 1266 projects light onto a screen to display an image. For example, the screen may be located inside or outside the electronic device 1201.

The display 1260 may further include a control circuit for controlling the panel 1262, the hologram device 1264, or the projector 1266.

The interface 1270 may include a High-Definition Multimedia Interface (HDMI) 1272, a Universal Serial Bus (USB) 1274, an optical interface 1276, or a D-subminiature (D-sub) 1278. The interface 1270 may be included in the communication interface 170 illustrated in FIG. 1. Additionally or alternatively, the interface 1270 may include a Mobile High-definition Link (MHL) interface, a Secure Digital (SD) card/Multi-Media Card (MMC) interface, or an Infrared Data Association (IrDA) standard interface.

The audio module 1280 bilaterally converts a sound and an electrical signal. At least some components of the audio module 1280 may be included in the input/output interface 150 illustrated in FIG. 1. The audio module 1280 processes sound information input or output through a speaker 1282, a receiver 1284, earphones 1286, or the microphone 1288.

The camera module 1291 is a device which photographs a still image and/or a moving image. The camera module 291 may include one or more image sensors (for example, a front sensor or a back sensor), a lens, an Image Signal Processor (ISP) or a flash (for example, LED or xenon lamp).

The power management module 1295 manages power of the electronic device 1201. The power management module 1295 may include a Power Management Integrated Circuit (PMIC), a charger Integrated Circuit (IC), or a battery gauge. The PMIC may have a wired and/or wireless charging scheme. Examples of the wireless charging method include a magnetic resonance method, a magnetic induction method, an electromagnetic method, and the like. Additional circuits (e.g., a coil loop, a resonance circuit, a rectifier, etc.) for wireless charging may be further included. The battery gauge measures a remaining amount, a charging voltage and current, or temperature of a battery 1296.

The battery 1296 may include a rechargeable battery and/or a solar battery.

The indicator 797 shows particular statuses of the electronic device 1201 or a part (for example, AP 1210) of the electronic device 1201, for example, a boot-up status, a message status, a charging status, etc.

The motor 1298 converts an electrical signal into mechanical vibrations, and generates a vibration or haptic effect.

The electronic device 1201 may include a processing device (for example, a GPU) for supporting mobile TV. The processing device for supporting mobile TV processes media data according to a standard of Digital Multimedia Broadcasting (DMB), Digital Video Broadcasting (DVB), media flow, etc.

Each of the above-described component elements of hardware according to the present disclosure may be configured with one or more components, and the names of the corresponding component elements may vary based on the type of electronic device. The electronic device, according to various embodiments of the present disclosure, may include at least one of the aforementioned elements. Some elements may be omitted or other additional elements may be further included in the electronic device. Further, some of the components of the electronic device, according to the various embodiments of the present disclosure, may be combined to form a single entity, and thus, may equivalently execute functions of the corresponding elements prior to the combination.

The embodiments disclosed herein are provided merely to easily describe technical details of the present disclosure and to help in an understanding of the present disclosure, and are not intended to limit the scope of the present disclosure. Accordingly, the scope of the present disclosure should be construed as including all modifications or various other embodiments based on the technical idea of the present disclosure.

The various embodiments disclosed herein are provided merely to easily describe technical details of the present disclosure and to help in an understanding of the present disclosure, and are not intended to limit the scope of the present disclosure. Accordingly, the scope of the present disclosure should be construed as including all modifications or various other embodiments based on the technical idea of the present disclosure as defined by the following claims and their equivalents.

What is claimed is:

1. A method for batch processing of data between processors of an electronic device, the method comprising:
    transmitting, by a first processor, a request for batch processing to provide batch data to at least one application, to a second processer, wherein the request includes at least one of information of the batch data and a batch processing trigger condition including target data to be used for determining a batch processing period for the batch processing;
    identifying, by the second processor, the target data from data acquired using one or more sensors in response to the request;
    determining, by the second processor, the batch processing period based on the identified target data and the batch processing trigger condition;
    transmitting, by the second processor, the batch data generated to include at least a part of the acquired data according to the determined batch processing period, to the first processor; and
    providing, by the first processor, the received batch data from the second processor to the at least one application.

2. The method of claim 1, wherein the at least one application provides an exercise goal service, and
    wherein the exercise goal service sets a goal corresponding to at least one of exercise time, exercise distance, number of steps, calories to burn, and exercise state recognition, determines whether the set goal is accomplished, and provides a notification.

3. The method of claim 1, wherein the information of the batch data includes a type of data required for batch processing of the at least one application.

4. The method of claim 3, wherein the type of data includes at least one of sensing data which is collected from the one or more sensors acquired by the second processor and context data which is calculated using the sensing data.

5. The method of claim 1, wherein the batch processing trigger condition includes at least one of a type of the target data and a scheme of determining the batch processing period.

6. The method of claim 5, wherein the scheme of determining the batch processing period includes at least one of a first threshold value of accumulated time based on an acquisition of the target data, a second threshold value of an amount of accumulated data based on the acquisition of the target data, and a third threshold value of a number of pieces of the accumulated data based on the batch processing.

7. The method of claim 6, wherein different threshold values are set according to the type of the target data in the scheme of determining the batch processing period.

8. The method of claim 1, wherein the acquired data includes at least one of sensing data acquired by the sensor based on the request and context data calculated using the sensing data based on the request.

9. The method of claim 1, wherein the batch processing period includes at least one of a first batch processing period and a second batch processing period.

10. The method of claim 9, wherein the first batch processing period is at least one of a preset period and a point at which a preset amount of data for batch processing is accumulated, and
wherein the second batch processing period is at least one of a selectively modified setting of a batch processing period and a point at which selectively modified setting of a amount of data for batch processing is accumulated.

11. The method of claim 10, wherein the second batch processing period is selectively set based on the identified target data and the batch processing trigger condition.

12. The method of claim 1, wherein the batch processing period is determined based on at least one of whether the target data is acquired, accumulated time based on an acquisition of the target data reaches to a first threshold value, an amount of accumulated data based on the acquisition of the target data reaches to a second threshold value, and a number of pieces of the accumulated data based on the batch processing reaches to a third threshold value.

13. A first processor for batch processing of data between the first processor and a second processor of an electronic device, the first processor comprising:
at least one application; and
a batch processing controller configured to:
transmit a request for batch processing to provide batch data to the at least one application, to the second processor, wherein the request includes at least one of information of the batch data and a batch processing trigger condition including target data to be used for determining a batch processing period for the batch processing,
receive, from the second processor, the batch data generated to include at least a part of data acquired using one or more sensors according to the batch processing period determined by the second processor, and
provide the received batch data to the at least one application.

14. The first processor of claim 13, wherein the at least one application provides an exercise goal service, and
wherein the exercise goal service sets a goal corresponding to at least one of exercise time, exercise distance, number of steps, calories to burn, and exercise state recognition, determines whether the set goal is accomplished, and provides a notification.

15. The first processor of claim 13, wherein the information of the batch data includes a type of data required for batch processing of the at least one application.

16. The first processor of claim 15, wherein the type of data includes at least one of sensing data which is collected from the one or more sensors acquired by the second processor and context data which is calculated using the sensing data.

17. The first processor of claim 13, wherein the batch processing trigger condition includes at least one of a type of the target data and a scheme of determining the batch processing period.

18. The first processor of claim 17, wherein the scheme of determining the batch processing period includes at least one of a first threshold value of accumulated time based on an acquisition of the target data, a second threshold value of an amount of accumulated data based on the acquisition of the target data, and a third threshold value of a number of pieces of the accumulated data based on batch processing of the acquired data.

19. The first processor of claim 18, wherein different threshold values are set according to the type of the target data in the scheme of determining the batch processing period.

20. A second processor for batch processing of data between a first processor and the second processor of an electronic device, the second processor comprising:
a data module configured to store data acquired by one or more sensors; and
a batch data trigger module configured to:
receive, from the first processor, a request for batch processing to provide batch data to at least one application, wherein the request includes at least one of information of the batch data and a batch processing trigger condition including target data to be used for determining a batch processing period for the batch processing,
identify the target data from data acquired using one or more sensors in response to the request,
determine the batch processing period based on the identified target data and the batch processing trigger condition, and
transmit, to the first processor, the batch data generated to include at least a part of the acquired data according to the determined batch processing period.

21. The second processor of claim 20, wherein the data module is configured to select and acquire data based on the request, and store the acquired data.

22. The second processor of claim 21, wherein the data module is configured to collect sensing data from the one or more sensors based on the request, and calculate context data using the sensing data.

23. The second processor of claim 20, wherein the batch processing period includes at least one of a first batch processing period and a second batch processing period.

24. The second processor of claim 23, wherein the first batch processing period is at least one of a preset period and a point at which a preset amount of data for batch processing is accumulated, and
wherein the second batch processing period is at least one of a selectively modified setting of a batch processing period and a point at which selectively modified setting of a amount of data for batch processing is accumulated.

25. The second processor of claim 24, wherein the second batch processing period is selectively set according to the identified target data and the batch processing trigger condition.

26. The second processor of claim 20, wherein the batch data trigger module is configured to determine based on at least one of whether the target data is acquired, accumulated time based on an acquisition of the target data reaches to a first threshold value, an amount of accumulated data based on the acquisition of the target data reaches to a second threshold value, and a number of pieces of the accumulated data based on the batch processing reaches to a third threshold value.

* * * * *